(12) United States Patent
Greene et al.

(10) Patent No.: US 8,110,659 B1
(45) Date of Patent: Feb. 7, 2012

(54) HUMAN TUMOR NECROSIS FACTOR RECEPTOR-LIKE GENES

(75) Inventors: John M. Greene, Gaithersburg, MD (US); Robert D. Fleischmann, Gaithersburg, MD (US); Jian Ni, Rockville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 08/718,737

(22) Filed: Sep. 18, 1996

Related U.S. Application Data

(63) Continuation-in-part of application No. 08/469,637, filed on Jun. 6, 1995, now Pat. No. 7,094,564, which is a continuation-in-part of application No. PCT/US95/03216, filed on Mar. 15, 1995.

(51) Int. Cl.
*C07K 14/00* (2006.01)
(52) U.S. Cl. .................................................. 530/350
(58) Field of Classification Search .................. 530/350; 435/69.1
See application file for complete search history.

(56) References Cited

U.S. PATENT DOCUMENTS

| 5,395,760 A | 3/1995 | Smith et al. | 435/240.1 |
| 5,464,938 A | 11/1995 | Smith et al. | 530/350 |
| 5,712,155 A * | 1/1998 | Smith et al. | 435/320.1 |
| 5,741,899 A * | 4/1998 | Capon et al. | 536/23.4 |

FOREIGN PATENT DOCUMENTS

| EP | 0 585 939 | 3/1994 |
| EP | 0 816 380 A | 1/1998 |
| WO | WO 91/09045 | 6/1991 |
| WO | WO 94/09137 | 4/1994 |
| WO | WO 94/13808 | 6/1994 |
| WO | WO96/28546 | 2/1996 |
| WO | WO96/26217 | 8/1996 |

OTHER PUBLICATIONS

Crowe et al. (1994) Science 264 : 707-710.*
Beutler et al. (1994) Science 264 : 667-668.*
Smith et al. (1990) Science 248 : 1019-1023.*
Bowie et al. (1990) Science 247 : 1306-1310.*
Salgaller et al. (1994) Cancer Immunol. Immunother. 39 : 105-116.*
George et al. (1988) Macromolecular Sequencing and Synthegsis (ED. By D. H. Schlessinger) Alan R. Liss , Inc., New York, pp. 127-149.*
Aggarwal, B. B. and K. Natarajan, "Tumor necrosis factors: Developments during the last decade," *Eur. Cytokine Netw.* 7(2):93-124 (Apr.-Jun. 1996).
Camerini, D. et al., "The T Cell Activation Antigen CD27 Is a Member of the Nerve Growth Factor/Tumor Necrosis Factor Receptor Gene Family," *J. Immunol.* 147(9):3165-3169 (1991).
Dürkop, H. et al., "Molecular Cloning and Expression of a New Member of the Nerve Growth Factor Receptor Family That Is Characteristic for Hodgkin's Disease," *Cell* 68:421-427 (1992).

Engelmann, H. et al., "Two Tumor Necrosis Factor-binding Proteins Purified from Human Urine. Evidence for Immunological Cross-reactivity with Cell Surface Tumor Necrosis Factor Receptors," *J. Biol. Chem.* 265(3):1531-1536 (1990).
Himmler, A. et al., "Molecular Cloning and Expression of Human and Rat Tumor Necrosis Factor Receptor Chain (p60) and Its Soluble Derivative, Tumor Necrosis Factor-Binding Protein," *DNA and Cell Biol.* 9(10):705-715 (1990).
Hohmann, H.-P. et al., "Two Different Cell Types Have Different Major Receptors for Human Tumor Necrosis Factor (TNFα)" *J. Biol. Chem.* 264(25):14927-14934 (1989).
Hsu, K. C. and M. V. Chao, "Differential Expression and Ligand Binding Properties of Tumor Necrosis Factor Receptor Chimeric Mutants," *J. Biol. Chem.* 268(22):16430-16436 (1993).
Itoh, N. et al., "The Polypeptide Encoded by the cDNA for Human Cell Surface Antigen Fas Can Mediate Apoptosis," *Cell* 66:233-243 (1991).
Johnson, D. et al., "Expression and Structure of the Human NGF Receptor," *Cell* 47:545-554 (1986).
Loetscher, H. et al., "Molecular Cloning and Expression of the Human 55 kd Tumor Necrosis Factor Receptor," *Cell* 61:351-359 (1990).
Mallett, S. et al., "Characterization of the MRC 0X40 antigen of activated CD4 positive T Lymphocytes—a molecule related to nerve growth factor receptor," *EMBO J.* 9(4):1063-1068 (1990).
Nophar, Y. et al., "Soluble forms of tumor necrosis factor receptors (TNF-Rs). The cDNA for the type I TNF-R, cloned using amino acid sequence data of its soluble form, encodes both the cell surface and a soluble form of the receptor," *EMBO J.* 9(10):3269-3278 (1990).
Pfeffer, K. et al., "Mice Deficient for the 55 kd Tumor Necrosis Factor Receptor Are Resistant to Endotoxic Shock, yet Succumb to L. monocytogenes Infection," *Cell* 73:457-467 (1993).
Piguet, P. F. et al., "Evolution of collagen arthritis in mice is arrested by treatment with anti-tumour necrosis factor (TNF) antibody or a recombinant soluble TNF receptor," *Immunol.* 77:510-514 (1992).
Radeke, M. J. et al., "Gene transfer and molecular cloning of the rat nerve growth factor receptor," *Nature* 325:593-597 (1987).
Smith, C. A. et al., "T2 Open Reading Frame from the Shope Fibroma Virus Encodes a Soluble Form of the TNF Receptor," *Biochem. Biophys. Res. Comm.* 176(1):335-342 (1991).
Stamenkovic, I. et al., "A B-lymphocyte activation molecule related to the nerve growth factor receptor and induced by cytokines in carcinomas," *EMBO J.* 8(5):1403-1410 (1989).
Van Ostade, X. et al., "Human tumor necrosis factor mutants with preferential binding to and activity on either the R55 or R75 receptor," *Eur. J. Biochem.* 220(3):771-779 (Mar. 1994).
Chinnaiyan, A.M. et al., "Signal Transduction by DR3, a Death Domain-Containing Receptor Related to TNFR-1 and CD95," *Science* 274:990-992 (Nov. 1996).
Feinstein, E. et al., "The death domain: a module shared by proteins with diverse cellular functions," *TIBS* 20:342-344 (Sep. 1995).
Glasgow, E. and Schechter, N., Database EMBL-new3 on MASPAR, Accession No. L23876 (1993).

(Continued)

*Primary Examiner* — Michael Pak

(57) ABSTRACT

The present inventors have discovered novel receptors in the Tumor Necrosis Factor (TNF) receptor family. In particular, receptors having homology to the type 2 TNF receptor (TNF-RII) are provided. Isolated nucleic acid molecules are also provided encoding the novel receptors of the present invention. Receptor polypeptides are further provided as are vectors, host cells and recombinant methods for producing the same.

11 Claims, 11 Drawing Sheets

OTHER PUBLICATIONS

Lewis, M. et al., "Cloning and expression of cDNAs for two distinct murine tumor necrosis factor receptors demonstrate one receptor is species specific," *Proc. Natl. Acad. Sci. USA* 88:2830-2834 (1991).

Muzio, M. et al., "FLICE, A Novel FADD-Homologous ICE/CED-3-like Protease, Is Recruited to the CD95 (Fas/APO-1) Death-Inducing Signaling Complex," *Cell* 85:817-827 (Jun. 1996).

NCBI Entrez, GenBank Report, Accession No. D62967, from Fujiwara, T. et al. (Aug. 1995).

NCBI Entrez, GenBank Report, Accession No. D63118, from Fujiwara, T. et al. (Aug. 1995).

NCBI Entrez, GenBank Report, Accession No. D63125, from Fujiwara, T. et al. (Aug. 1995).

NCBI Entrez, GenBank Report, Accession No. D63126, from Fujiwara, T. et al. (Aug. 1995).

NCBI Entrez, GenBank Report, Accession No. AA296905, from Adams, M.D. et al. (Sep. 1995).

NCBI Entrez, GenBank Report, Accession No. AA296908, from Adams, M.D. et al. (Sep. 1995).

NCBI Entrez, GenBank Report, Accession No. 298429, from Adams, M.D. et al. (Sep. 1995).

NCBI Entrez, GenBank Report, Accession No. H88769, from Hillier, L. et al. (Nov. 1995).

NCBI Entrez, GenBank Report, Accession No. C02463, from Okubo, K. et al. (Jul. 1996).

NCBI Entrez, GenBank Report, Accession No. AA037313, from Hillier, L. et al. (Nov. 1996).

NCBI Entrez, GenBank Report, Accession No. AA195113, from Hillier, L. et al. (May 1997).

NCBI Entrez, GenBank Report, Accession No. AA233719, from Hillier, L. et al. (Aug. 1997).

NCBI Entrez, GenBank Report, Accession No. AA706996, from Hillier, L. et al. (Dec. 1997).

NCBI Entrez, GenBank Report, Accession No. AA599841, from Jia, L. et al. (Mar. 1998).

Aruffo, A.A., et al., Database A-Geneseq24 on MASPAR, Accession No. R38859 (1993).

Aslanidis, C., Database EMBL-new3 on MASPAR, Accession No. X75491 (Mar. 1994).

Genexpress, Database EMBL/Genbank/DDBJ on MASPAR, Accession No. L23876 (1993).

Glasgow, E. and Schechter, N., Database EMBL-new3 on MASPAR, Accession No. L23876 (1993).

Hillier, L., et al., Database EST-STS on MASPAR, Accession No. H14106 (Jul. 1995).

Hudson, T., Database EST-STS on MASPAR, Accession No. G11923 (Oct. 1995).

Zauner, W., et al., Database EMBL-new3 on MASPAR, Accession No. X60370, X60371, X60550 (1992).

Kwon et al. "TR1, a new member of the tumor necrosis factor receptor superfamily, induces fibroblast proliferation and inhibits osteoclastogenesis and bone resorption" FASEB Journal 12(10):845-854 (1998).

Simonet et al. "Osteoprotegerin: A novel secreted protein involved in the regulation of bone density" Cell 89(2):309-319 (1997).

Tsuda et al. "Isolation of a novel cytokine from human fibroblasts that specifically inhibits osteoclastogenesis" Biochemical and Biophysical Res. Comms. 234(1):137-142 (1997).

* cited by examiner

```
                  10                  30                   50
        CGCCCAGCCGCCGCCTCCAAGCCCCTGAGGTTTCCGGGGACCACAATGAACAAGTTGCTG
                                                          M  N  K  L  L
                  70                  90                  110
        TGCTGCGCGCTCGTGTTTCTGGACATCTCCATTAAGTGGACCACCCAGGAAACGTTTCCT
         C  C  A  L  V  F  L  D  I  S  I  K  W  T  T  Q  E  T  F  P
                 130                 150                  170
        CCAAAGTACCTTCATTATGACGAAGAAACCTCTCATCAGCTGTTGTGTGACAAATGTCCT
         P  K  Y  L  H  Y  D  E  E  T  S  H  Q  L  L  C  D  K  C  P
                 190                 210                  230
        CCTGGTACCTACCTAAAACAACACTGTACAGCAAAGTGGAAGACCGTGTGCGCCCCTTGC
         P  G  T  Y  L  K  Q  H  C  T  A  K  W  K  T  V  C  A  P  C
                 250                 270                  290
        CCTGACCACTACTACACAGACAGCTGGCACACCAGTGACGAGTGTCTATACTGCAGCCCC
         P  D  H  Y  Y  T  D  S  W  H  T  S  D  E  C  L  Y  C  S  P
                 310                 330                  350
        GTGTGCAAGGAGCTGCAGTACGTCAAGCAGGAGTGCAATCGCACCCACAACCGCGTGTGC
         V  C  K  E  L  Q  Y  V  K  Q  E  C  N  R  T  H  N  R  V  C
                 370                 390                  410
        GAATGCAAGGAAGGGCGCTACCTTGAGATAGAGTTCTGCTTGAAACATAGGAGCTGCCCT
         E  C  K  E  G  R  Y  L  E  I  E  F  C  L  K  H  R  S  C  P
                 430                 450                  470
        CCTGGATTTGGAGTGGTGCAAGCTGGAACCCCAGAGCGAAATACAGTTTGCAAAAGATGT
         P  G  F  G  V  V  Q  A  G  T  P  E  R  N  T  V  C  K  R  C
                 490                 510                  530
        CCAGATGGGTTCTTCTCAAATGAGACGTCATCTAAAGCACCCTGTAGAAAACACACAAAT
         P  D  G  F  F  S  N  E  T  S  S  K  A  P  C  R  K  H  T  N
                 550                 570                  590
        TGCAGTGTCTTTGGTCTCCTGCTAACTCAGAAAGGAAATGCAACACACGACAACATATGT
         C  S  V  F  G  L  L  L  T  Q  K  G  N  A  T  H  D  N  I  C
                 610                 630                  650
        TCCGGAAACAGTGAATCAACTCAAAAATGTGGAATAGATGTTACCCTGTGTGAGGAGGCA
         S  G  N  S  E  S  T  Q  K  C  G  I  D  V  T  L  C  E  E  A
                 670                 690                  710
        TTCTTCAGGTTTGCTGTTCCTACAAAGTTTACGCCTAACTGGCTTAGTGTCTTGGTAGAC
         F  F  R  F  A  V  P  T  K  F  T  P  N  W  L  S  V  L  V  D
                 730                 750                  770
        AATTTGCCTGGCACCAAAGTAAACGCAGAGAGTGTAGAGAGGATAAAACGGCAACACAGC
         N  L  P  G  T  K  V  N  A  E  S  V  E  R  I  K  R  Q  H  S
                 790                 810                  830
        TCACAAGAACAGACTTTCCAGCTGCTGAAGTTATGGAAACATCAAAACAAAGACCAAGAT
         S  Q  E  Q  T  F  Q  L  L  K  L  W  K  H  Q  N  K  D  Q  D
                 850                 870                  890
        ATAGTCAAGAAGATCATCCAAGATATTGACCTCTGTGAAAACAGCGTGCAGCGGCACATT
         I  V  K  K  I  I  Q  D  I  D  L  C  E  N  S  V  Q  R  H  I
                 910                 930                  950
        GGACATGCTAACCTCACCTTCGAGCAGCTTCGTAGCTTGATGGAAAGCTTACCGGGAAAG
         G  H  A  N  L  T  F  E  Q  L  R  S  L  M  E  S  L  P  G  K
                 970                 990                 1010
        AAAGTGGGAGCAGAAGACATTGAAAAAACAATAAAGGCATGCAAACCCAGTGACCAGATC
         K  V  G  A  E  D  I  E  K  T  I  K  A  C  K  P  S  D  Q  I
                1030                1050                 1070
        CTGAAGCTGCTCAGTTTGTGGCGAATAAAAAATGGCGACCAAGACACCTTGAAGGGCCTA
         L  K  L  L  S  L  W  R  I  K  N  G  D  Q  D  T  L  K  G  L
                1090                1110                 1130
        ATGCACGCACTAAAGCACTCAAAGACGTACCACTTTCCCAAAACTGTCACTCAGAGTCTA
```

FIGURE 1(A)

```
     M   H   A   L   K   H   S   K   T   Y   H   F   P   K   T   V   T   Q   S   L
            1150                1170                1190
AAGAAGACCATCAGGTTCCTTCACAGCTTCACAATGTACAAATTGTATCAGAAGTTATTT
     K   K   T   I   R   F   L   H   S   F   T   M   Y   K   L   Y   Q   K   L   F
            1210                1230                1250
TTAGAAATGATAGGTAACCAGGTCCAATCAGTAAAAATAAGCTGCTTATAACTGGAAATG
     L   E   M   I   G   N   Q   V   Q   S   V   K   I   S   C   L   *
            1270                1290                1310
GCCATTGAGCTGTTTCCTCACAATTGGCGAGATCCCATGGATGAGTAAACTGTTTCTCAG
            1330                1350                1370
GCACTTGAGGCTTTCAGTGATATCTTTCTCATTACCAGTGACTAATTTTGCCACAGGGTA
            1390                1410                1430
CTAAAAGAAACTATGATGTGGAGAAAGGACTAACATCTCCTCCAATAAACCCCAAATGGT
            1450                1470                1490
TAATCCAACTGTCAGATCTGGATCGTTATCTACTGACTATATTTTCCCTTATTACTGCTT
            1510
GCAGTAATTCAACTGGAAAAAAAAAAA
```

FIGURE 1(B)

```
       10                  30                  50
ATGAACAAGTTGCTGTGCTGCGCGCTCGTGTTTCTGGACATCTCCATTAAGTGGACCACC
 M  N  K  L  L  C  C  A  L  V  F  L  D  I  S  I  K  W  T  T
       70                  90                 110
CAGGAAACGTTTCCTCCAAAGTACCTTCATTATGACGAAGAAACCTCTCATCAGCTGTTG
 Q  E  T  F  P  P  K  Y  L  H  Y  D  E  E  T  S  H  Q  L  L
      130                 150                 170
TGTGACAAATGTCCTCCTGGTACCTACCTAAAACAACACTGTACAGCAAAGTGGAAGACC
 C  D  K  C  P  P  G  T  Y  L  K  Q  H  C  T  A  K  W  K  T
      190                 210                 230
GTGTGCGCCCCTTGCCCTGACCACTACTACACAGACAGCTGGCACACCAGTGACGAGTGT
 V  C  A  P  C  P  D  H  Y  Y  T  D  S  W  H  T  S  D  E  C
      250                 270                 290
CTATACTGCAGCCCCGTGTGCAAGGAGCTGCAGTACGTCAAGCAGGAGTGCAATCGCACC
 L  Y  C  S  P  V  C  K  E  L  Q  Y  V  K  Q  E  C  N  R  T
      310                 330                 350
CACAACCGCGTGTGCGAATGCAAGGAAGGGCGCTACCTTGAGATAGAGTTCTGCTTGAAA
 H  N  R  V  C  E  C  K  E  G  R  Y  L  E  I  E  F  C  L  K
      370                 390                 410
CATAGGAGCTGCCCTCCTGGATTTGGAGTGGTGCAAGCTGGAACCCCAGAGCGAAATACA
 H  R  S  C  P  P  G  F  G  V  V  Q  A  G  T  P  E  R  N  T
      430                 450                 470
GTTTGCAAAAGATGTCCAGATGGGTTCTTCTCAAATGAGACGTCATCTAAAGCACCCTGT
 V  C  K  R  C  P  D  G  F  F  S  N  E  T  S  S  K  A  P  C
      490                 510                 530
AGAAAACACACACAAATTGCAGTGTCTTTGGTCTCCTGCTAACTCAGAAAGGAAATGCAACA
 R  K  H  T  N  C  S  V  F  G  L  L  L  T  Q  K  G  N  A  T
      550                 570                 590
CACGACAACATATGTTCCGGAAACAGTGAATCAACTCAAAAATGTGGAATAGATGTTACC
 H  D  N  I  C  S  G  N  S  E  S  T  Q  K  C  G  I  D  V  T
      610                 630                 650
CTGTGTGAGGAGGCATTCTTCAGGTTTGCTGTTCCTACAAAGTTTACGCCTAACTGGCTT
 L  C  E  E  A  F  F  R  F  A  V  P  T  K  F  T  P  N  W  L
      670                 690                 710
AGTGTCTTGGTAGACAATTTGCCTGGCACCAAAGTAAACGCAGAGAGTGTAGAGAGGATA
 S  V  L  V  D  N  L  P  G  T  K  V  N  A  E  S  V  E  R  I
      730                 750                 770
AAACGGCAACACAGCTCACAAGAACAGACTTTCCAGCTGCTGAAGTTATGGAAACATCAA
 K  R  Q  H  S  S  Q  E  Q  T  F  Q  L  L  K  L  W  K  H  Q
      790                 810                 830
AACAAAGACCAAGATATAGTCAAGAAGATCATCCAAGATATTGACCTCTGTGAAAACAGC
 N  K  D  Q  D  I  V  K  K  I  I  Q  D  I  D  L  C  E  N  S
      850                 870                 890
GTGCAGCGGCACATTGGACATGCTAACCTCACCTTCGAGCAGCTTCGTAGCTTGATGGAA
 V  Q  R  H  I  G  H  A  N  L  T  F  E  Q  L  R  S  L  M  E
      910                 930                 950
AGCTTACCGGGAAAGAAAGTGGGAGCAGAAGACATTGAAAAAACAATAAAGGCATGCAAA
 S  L  P  G  K  K  V  G  A  E  D  I  E  K  T  I  K  A  C  K
      970                 990                1010
CCCAGTGACCAGATCCTGAAGCTGCTCAGTTTGTGGCGAATAAAAAATGGCGACCAAGAC
 P  S  D  Q  I  L  K  L  L  S  L  W  R  I  K  N  G  D  Q  D
     1030                1050                1070
ACCTTGAAGGGCCTAATGCACGCACTAAAGCACTCAAAGACGTACCACTTTCCCAAAACT
 T  L  K  G  L  M  H  A  L  K  H  S  K  T  Y  H  F  P  K  T
     1090                1110                1130
GTCACTCAGAGTCTAAAGAAGACCATCAGGTTCCTTCACAGCTTCACAATGTACAAATTG
 V  T  Q  S  L  K  K  T  I  R  F  L  H  S  F  T  M  Y  K  L
     1150                1170
```

FIGURE 2(A)

```
TATCAGAAGTTATTTTTAGAAATGATAGGTAATCTAGAAAAGATCTAA
 Y  Q  K  L  F  L  E  M  I  G  N  L  E  K  I
```

FIGURE 2(B)

```
  1 .....MNKLLCCALVFLDISIKWTTQETFPP.........KYLHYDEETS  36
         :   |..:|  ::.. .  :..| .|.|       :. .| ::|.
  1 MAPVAVWAALAVGLELWAAAHALPAQVAFTPYAPEPGSTCRLREYYDQTA  50

37 HQLLCDKCPPGTYLKQHCTAKWKTVCAPCPDHYYTDSWHTSDECLYCSPV  86
    |: |.||.|| . |  || ...|||..|.| ||: |: .||| |:.
 51 .QMCCSKCSPGQHAKVFCTKTSDTVCDSCEDSTYTQLWNWVPECLSCGSR  99

87 CKELQYVKQECNRTHNRVCECKEGRYLEIE......FCLKHRSCPPGFGV 130
    |.. |  .|.|.|.:||:|.|:.|:|  .:.    :| . |.|.|||||
100 CSSDQVETQACTREQNRICTCRPGWYCALSKQEGCRLCAPLRKCRPGFGV 149

131 VQAGTPERNTVCKRCPDGFFSNETSSKAPCRKHTNCSVFGLLLTQKGNAT 180
    ..:||...:.|||.|:.| |||.|||.. ||.| |.|.:: .|||.
150 ARPGTETSDVVCKPCAPGTFSNTTSSTDICRPHQICNVVAI....PGNAS 195

181 HDNIC..................SGNSESTQKCGIDVTLCEEAFF...  207
    |.:|                   |..|: ||... . | ....|:
196 MDAVCTSTSPTRSMAPGAVHLPQPVSTRSQHTQPTPEPSTAPSTSFLLPM 245

208 ..........RFAVPTKFTPNWLSVLVDNLPGTKVNAESVERIKR....  242
              ||:|. :... . :: | . ||. :..:|:
246 GPSPPAEGSTGDFALPVGLIVG..VTALGLLIIGVVNCVIMTQVKKKPLC 293

243 .QHSSQEQTFQLLKLWKHQNKDQDIV.....KKIIQDIDLCENSVQRHIG 286
    |:... . :.  | : |..:|: :     ..  .:: :...::|: .
294 LQREAKVPHLPADKARGTQGPEQQHLLITAPSSSSSSLESSASALDRRAP 343

287 HANLTFEQLRSLMESLPGK...KVGAEDIEKTIKACKPSDQILKLLSLWR 333
    | . |  |.::.| :|.  ..|..|  ... .:....  .:   ::  ..
344 TRNQP..QAPGVEASGAGEARASTGSSDSSPGGHGTQVNVTCIVNVCSSS 391

334 IKNGDQDTLKGLMHALKHSKTYHFPKTVTQSLKKTIRFLHS.....FTMY 378
    ..:: ..   :   : ..|.. . ||. .:.|.  ::|     |:.
392 DHSSQCSSQASSTMGDTDSSPSESPKDEQVPFSKEECAFRSQLETPETLL 441

379 KLYQKLFLEMIGNQVQSVKISCL. 401
    :. |.: | . .::|| |  |
442 GSTEEKPLPL.GVPDAGMKPS... 461
```

FIGURE 3

ELISA Assay (plate coated with mAb to sTNFR I or STNFR II)

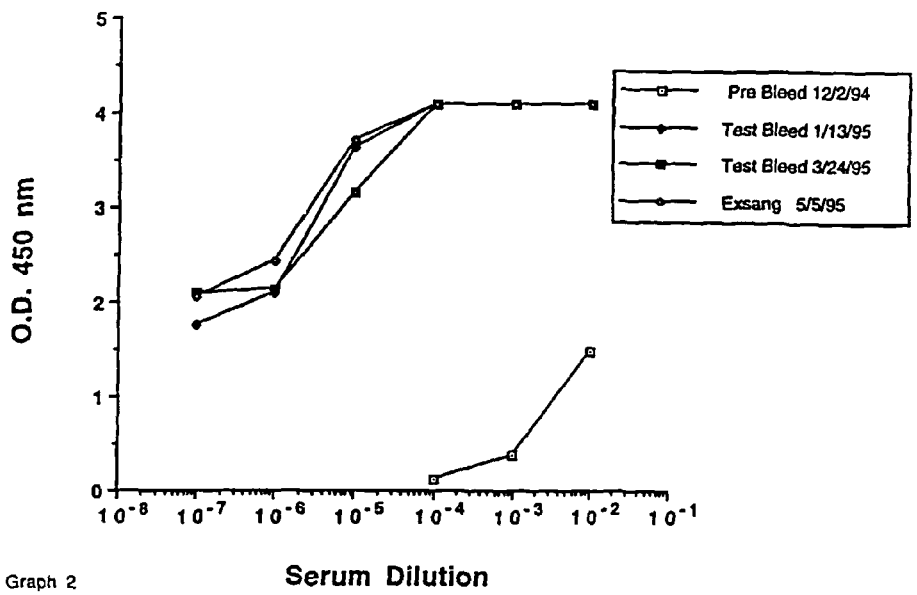
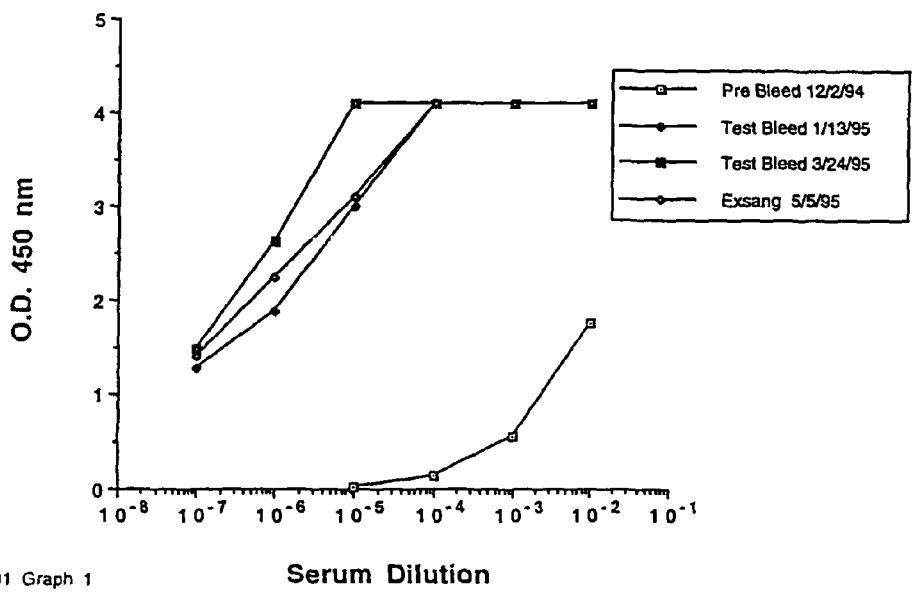
FIGURE 9

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 1527 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 46..1248

(ix) FEATURE:
      (A) NAME/KEY: sig_peptide
      (B) LOCATION: 46..106

(ix) FEATURE:
      (A) NAME/KEY: mat_peptide
      (B) LOCATION: 109..1248

(xi) SEQUENCE DESCRIPTION: SEQ ID NO:1:

```
CGCCCAGCCG CCGCCTCCAA GCCCCTGAGG TTTCCGGGGA CCACA ATG AAC AAG            54
                                              Met Asn Lys
                                              -21 -20

TTG CTG TGC TGC GCG CTC GTG TTT CTG GAC ATC TCC ATT AAG TGG ACC         102
Leu Leu Cys Cys Ala Leu Val Phe Leu Asp Ile Ser Ile Lys Trp Thr
            -15              -10                  -5

ACC CAG GAA ACG TTT CCT CCA AAG TAC CTT CAT TAT GAC GAA GAA ACC         150
Thr Gln Glu Thr Phe Pro Pro Lys Tyr Leu His Tyr Asp Glu Glu Thr
              1               5                  10

TCT CAT CAG CTG TTG TGT GAC AAA TGT CCT CCT GGT ACC TAC CTA AAA         198
Ser His Gln Leu Leu Cys Asp Lys Cys Pro Pro Gly Thr Tyr Leu Lys
 15              20                  25                  30

CAA CAC TGT ACA GCA AAG TGG AAG ACC GTG TGC GCC CCT TGC CCT GAC         246
Gln His Cys Thr Ala Lys Trp Lys Thr Val Cys Ala Pro Cys Pro Asp
                 35                  40                  45

CAC TAC TAC ACA GAC AGC TGG CAC ACC AGT GAC GAG TGT CTA TAC TGC         294
His Tyr Tyr Thr Asp Ser Trp His Thr Ser Asp Glu Cys Leu Tyr Cys
                 50                  55                  60

AGC CCC GTG TGC AAG GAG CTG CAG TAC GTC AAG CAG GAG TGC AAT CGC         342
Ser Pro Val Cys Lys Glu Leu Gln Tyr Val Lys Gln Glu Cys Asn Arg
             65                  70                  75

ACC CAC AAC CGC GTG TGC GAA TGC AAG GAA GGG CGC TAC CTT GAG ATA         390
Thr His Asn Arg Val Cys Glu Cys Lys Glu Gly Arg Tyr Leu Glu Ile
         80                  85                  90

GAG TTC TGC TTG AAA CAT AGG AGC TGC CCT CCT GGA TTT GGA GTG GTG         438
Glu Phe Cys Leu Lys His Arg Ser Cys Pro Pro Gly Phe Gly Val Val
 95                 100                 105                 110

CAA GCT GGA ACC CCA GAG CGA AAT ACA GTT TGC AAA AGA TGT CCA GAT         486
Gln Ala Gly Thr Pro Glu Arg Asn Thr Val Cys Lys Arg Cys Pro Asp
                115                 120                 125

GGG TTC TTC TCA AAT GAG ACG TCA TCT AAA GCA CCC TGT AGA AAA CAC         534
Gly Phe Phe Ser Asn Glu Thr Ser Ser Lys Ala Pro Cys Arg Lys His
                130                 135                 140

ACA AAT TGC AGT GTC TTT GGT CTC CTG CTA ACT CAG AAA GGA AAT GCA         582
Thr Asn Cys Ser Val Phe Gly Leu Leu Leu Thr Gln Lys Gly Asn Ala
            145                 150                 155
```

```
ACA CAC GAC AAC ATA TGT TCC GGA AAC AGT GAA TCA ACT CAA AAA TGT        630
Thr His Asp Asn Ile Cys Ser Gly Asn Ser Glu Ser Thr Gln Lys Cys
    160                 165                 170

GGA ATA GAT GTT ACC CTG TGT GAG GAG GCA TTC TTC AGG TTT GCT GTT        678
Gly Ile Asp Val Thr Leu Cys Glu Glu Ala Phe Phe Arg Phe Ala Val
175                 180                 185                 190

CCT ACA AAG TTT ACG CCT AAC TGG CTT AGT GTC TTG GTA GAC AAT TTG        726
Pro Thr Lys Phe Thr Pro Asn Trp Leu Ser Val Leu Val Asp Asn Leu
            195                 200                 205

CCT GGC ACC AAA GTA AAC GCA GAG AGT GTA GAG AGG ATA AAA CGG CAA        774
Pro Gly Thr Lys Val Asn Ala Glu Ser Val Glu Arg Ile Lys Arg Gln
        210                 215                 220

CAC AGC TCA CAA GAA CAG ACT TTC CAG CTG CTG AAG TTA TGG AAA CAT        822
His Ser Ser Gln Glu Gln Thr Phe Gln Leu Leu Lys Leu Trp Lys His
    225                 230                 235

CAA AAC AAA GAC CAA GAT ATA GTC AAG AAG ATC ATC CAA GAT ATT GAC        870
Gln Asn Lys Asp Gln Asp Ile Val Lys Lys Ile Ile Gln Asp Ile Asp
    240                 245                 250

CTC TGT GAA AAC AGC GTG CAG CGG CAC ATT GGA CAT GCT AAC CTC ACC        918
Leu Cys Glu Asn Ser Val Gln Arg His Ile Gly His Ala Asn Leu Thr
255                 260                 265                 270

TTC GAG CAG CTT CGT AGC TTG ATG GAA AGC TTA CCG GGA AAG AAA GTG        966
Phe Glu Gln Leu Arg Ser Leu Met Glu Ser Leu Pro Gly Lys Lys Val
            275                 280                 285

GGA GCA GAA GAC ATT GAA AAA ACA ATA AAG GCA TGC AAA CCC AGT GAC       1014
Gly Ala Glu Asp Ile Glu Lys Thr Ile Lys Ala Cys Lys Pro Ser Asp
        290                 295                 300

CAG ATC CTG AAG CTG CTC AGT TTG TGG CGA ATA AAA AAT GGC GAC CAA       1062
Gln Ile Leu Lys Leu Leu Ser Leu Trp Arg Ile Lys Asn Gly Asp Gln
    305                 310                 315

GAC ACC TTG AAG GGC CTA ATG CAC GCA CTA AAG CAC TCA AAG ACG TAC       1110
Asp Thr Leu Lys Gly Leu Met His Ala Leu Lys His Ser Lys Thr Tyr
    320                 325                 330

CAC TTT CCC AAA ACT GTC ACT CAG AGT CTA AAG AAG ACC ATC AGG TTC       1158
His Phe Pro Lys Thr Val Thr Gln Ser Leu Lys Lys Thr Ile Arg Phe
335                 340                 345                 350

CTT CAC AGC TTC ACA ATG TAC AAA TTG TAT CAG AAG TTA TTT TTA GAA       1206
Leu His Ser Phe Thr Met Tyr Lys Leu Tyr Gln Lys Leu Phe Leu Glu
            355                 360                 365

ATG ATA GGT AAC CAG GTC CAA TCA GTA AAA ATA AGC TGC TTA               1248
Met Ile Gly Asn Gln Val Gln Ser Val Lys Ile Ser Cys Leu
        370                 375                 380

TAACTGGAAA TGGCCATTGA GCTGTTTCCT CACAATTGGC GAGATCCCAT GGATGAGTAA      1308

ACTGTTTCTC AGGCACTTGA GGCTTTCAGT GATATCTTTC TCATTACCAG TGACTAATTT      1368

TGCCACAGGG TACTAAAAGA AACTATGATG TGGAGAAAGG ACTAACATCT CCTCCAATAA      1428

ACCCCAAATG GTTAATCCAA CTGTCAGATC TGGATCGTTA CTACTGACT ATATTTTCCC      1488

TTATTACTGC TTGCAGTAAT TCAACTGGAA AAAAAAAA                              1527

(2) INFORMATION FOR SEQ ID NO:2:

(i) SEQUENCE CHARACTERISTICS:
        (A) LENGTH: 401 amino acids
        (B) TYPE: amino acid
        (D) TOPOLOGY: linear (ii) MOLECULE TYPE: protein (xi) SEQUENCE DESCRIPTION: SEQ ID NO:2:

Met Asn Lys Leu Leu Cys Cys Ala Leu Val Phe Leu Asp Ile Ser Ile
-21 -20                 -15                 -10
```

```
Lys Trp Thr Thr Gln Glu Thr Phe Pro Pro Lys Tyr Leu His Tyr Asp
 -5               1               5                   10

Glu Glu Thr Ser His Gln Leu Leu Cys Asp Lys Cys Pro Pro Gly Thr
             15              20              25

Tyr Leu Lys Gln His Cys Thr Ala Lys Trp Lys Thr Val Cys Ala Pro
         30              35              40

Cys Pro Asp His Tyr Tyr Thr Asp Ser Trp His Thr Ser Asp Glu Cys
     45              50              55

Leu Tyr Cys Ser Pro Val Cys Lys Glu Leu Gln Tyr Val Lys Gln Glu
 60          65              70              75

Cys Asn Arg Thr His Asn Arg Val Cys Glu Cys Lys Glu Gly Arg Tyr
                 80              85              90

Leu Glu Ile Glu Phe Cys Leu Lys His Arg Ser Cys Pro Pro Gly Phe
             95              100             105

Gly Val Val Gln Ala Gly Thr Pro Glu Arg Asn Thr Val Cys Lys Arg
         110             115             120

Cys Pro Asp Gly Phe Phe Ser Asn Glu Thr Ser Ser Lys Ala Pro Cys
     125             130             135

Arg Lys His Thr Asn Cys Ser Val Phe Gly Leu Leu Leu Thr Gln Lys
 140             145             150             155

Gly Asn Ala Thr His Asp Asn Ile Cys Ser Gly Asn Ser Glu Ser Thr
                 160             165             170

Gln Lys Cys Gly Ile Asp Val Thr Leu Cys Glu Glu Ala Phe Phe Arg
             175             180             185

Phe Ala Val Pro Thr Lys Phe Thr Pro Asn Trp Leu Ser Val Leu Val
         190             195             200

Asp Asn Leu Pro Gly Thr Lys Val Asn Ala Glu Ser Val Glu Arg Ile
 205             210             215

Lys Arg Gln His Ser Ser Gln Glu Gln Thr Phe Gln Leu Leu Lys Leu
220             225             230             235

Trp Lys His Gln Asn Lys Asp Gln Asp Ile Val Lys Lys Ile Ile Gln
             240             245             250

Asp Ile Asp Leu Cys Glu Asn Ser Val Gln Arg His Ile Gly His Ala
         255             260             265

Asn Leu Thr Phe Glu Gln Leu Arg Ser Leu Met Glu Ser Leu Pro Gly
     270             275             280

Lys Lys Val Gly Ala Glu Asp Ile Glu Lys Thr Ile Lys Ala Cys Lys
 285             290             295

Pro Ser Asp Gln Ile Leu Lys Leu Leu Ser Leu Trp Arg Ile Lys Asn
300             305             310             315

Gly Asp Gln Asp Thr Leu Lys Gly Leu Met His Ala Leu Lys His Ser
             320             325             330

Lys Thr Tyr His Phe Pro Lys Thr Val Thr Gln Ser Leu Lys Lys Thr
         335             340             345

Ile Arg Phe Leu His Ser Phe Thr Met Tyr Lys Leu Tyr Gln Lys Leu
     350             355             360

Phe Leu Glu Met Ile Gly Asn Gln Val Gln Ser Val Lys Ile Ser Cys
 365             370             375

Leu
380

(2) INFORMATION FOR SEQ ID NO:3:

(i) SEQUENCE CHARACTERISTICS:
```

```
        (A) LENGTH: 1188 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1185

(ix) FEATURE:
        (A) NAME/KEY: sig_peptide
        (B) LOCATION: 1..61

(ix) FEATURE:
        (A) NAME/KEY: mat_peptide
        (B) LOCATION: 64..1185

(xi) SEQUENCE DESCRIPTION: SEQ ID NO:3:

ATG AAC AAG TTG CTG TGC TGC GCG CTC GTG TTT CTG GAC ATC TCC ATT        48
Met Asn Lys Leu Leu Cys Cys Ala Leu Val Phe Leu Asp Ile Ser Ile
-21 -20              -15                  -10

AAG TGG ACC ACC CAG GAA ACG TTT CCT CCA AAG TAC CTT CAT TAT GAC        96
Lys Trp Thr Thr Gln Glu Thr Phe Pro Pro Lys Tyr Leu His Tyr Asp
 -5               1               5                  10

GAA GAA ACC TCT CAT CAG CTG TTG TGT GAC AAA TGT CCT CCT GGT ACC       144
Glu Glu Thr Ser His Gln Leu Leu Cys Asp Lys Cys Pro Pro Gly Thr
                 15                  20                  25

TAC CTA AAA CAA CAC TGT ACA GCA AAG TGG AAG ACC GTG TGC GCC CCT       192
Tyr Leu Lys Gln His Cys Thr Ala Lys Trp Lys Thr Val Cys Ala Pro
         30                  35                  40

TGC CCT GAC CAC TAC TAC ACA GAC AGC TGG CAC ACC AGT GAC GAG TGT       240
Cys Pro Asp His Tyr Tyr Thr Asp Ser Trp His Thr Ser Asp Glu Cys
     45                  50                  55

CTA TAC TGC AGC CCC GTG TGC AAG GAG CTG CAG TAC GTC AAG CAG GAG       288
Leu Tyr Cys Ser Pro Val Cys Lys Glu Leu Gln Tyr Val Lys Gln Glu
 60                  65                  70                  75

TGC AAT CGC ACC CAC AAC CGC GTG TGC GAA TGC AAG GAA GGG CGC TAC       336
Cys Asn Arg Thr His Asn Arg Val Cys Glu Cys Lys Glu Gly Arg Tyr
                 80                  85                  90

CTT GAG ATA GAG TTC TGC TTG AAA CAT AGG AGC TGC CCT CCT GGA TTT       384
Leu Glu Ile Glu Phe Cys Leu Lys His Arg Ser Cys Pro Pro Gly Phe
         95                 100                 105

GGA GTG GTG CAA GCT GGA ACC CCA GAG CGA AAT ACA GTT TGC AAA AGA       432
Gly Val Val Gln Ala Gly Thr Pro Glu Arg Asn Thr Val Cys Lys Arg
     110                 115                 120

TGT CCA GAT GGG TTC TTC TCA AAT GAG ACG TCA TCT AAA GCA CCC TGT       480
Cys Pro Asp Gly Phe Phe Ser Asn Glu Thr Ser Ser Lys Ala Pro Cys
 125                 130                 135

AGA AAA CAC ACA AAT TGC AGT GTC TTT GGT CTC CTG CTA ACT CAG AAA       528
Arg Lys His Thr Asn Cys Ser Val Phe Gly Leu Leu Leu Thr Gln Lys
140                 145                 150                 155

GGA AAT GCA ACA CAC GAC AAC ATA TGT TCC GGA AAC AGT GAA TCA ACT       576
Gly Asn Ala Thr His Asp Asn Ile Cys Ser Gly Asn Ser Glu Ser Thr
                 160                 165                 170

CAA AAA TGT GGA ATA GAT GTT ACC CTG TGT GAG GAG GCA TTC TTC AGG       624
Gln Lys Cys Gly Ile Asp Val Thr Leu Cys Glu Glu Ala Phe Phe Arg
         175                 180                 185

TTT GCT GTT CCT ACA AAG TTT ACG CCT AAC TGG CTT AGT GTC TTG GTA       672
Phe Ala Val Pro Thr Lys Phe Thr Pro Asn Trp Leu Ser Val Leu Val
     190                 195                 200

GAC AAT TTG CCT GGC ACC AAA GTA AAC GCA GAG AGT GTA GAG AGG ATA       720
Asp Asn Leu Pro Gly Thr Lys Val Asn Ala Glu Ser Val Glu Arg Ile
 205                 210                 215
```

```
AAA CGG CAA CAC AGC TCA CAA GAA CAG ACT TTC CAG CTG CTG AAG TTA      768
Lys Arg Gln His Ser Ser Gln Glu Gln Thr Phe Gln Leu Leu Lys Leu
220                 225                 230                 235

TGG AAA CAT CAA AAC AAA GAC CAA GAT ATA GTC AAG AAG ATC ATC CAA      816
Trp Lys His Gln Asn Lys Asp Gln Asp Ile Val Lys Lys Ile Ile Gln
            240                 245                 250

GAT ATT GAC CTC TGT GAA AAC AGC GTG CAG CGG CAC ATT GGA CAT GCT      864
Asp Ile Asp Leu Cys Glu Asn Ser Val Gln Arg His Ile Gly His Ala
                255                 260                 265

AAC CTC ACC TTC GAG CAG CTT CGT AGC TTG ATG GAA AGC TTA CCG GGA      912
Asn Leu Thr Phe Glu Gln Leu Arg Ser Leu Met Glu Ser Leu Pro Gly
        270                 275                 280

AAG AAA GTG GGA GCA GAA GAC ATT GAA AAA ACA ATA AAG GCA TGC AAA      960
Lys Lys Val Gly Ala Glu Asp Ile Glu Lys Thr Ile Lys Ala Cys Lys
285                 290                 295

CCC AGT GAC CAG ATC CTG AAG CTG CTC AGT TTG TGG CGA ATA AAA AAT     1008
Pro Ser Asp Gln Ile Leu Lys Leu Leu Ser Leu Trp Arg Ile Lys Asn
300                 305                 310                 315

GGC GAC CAA GAC ACC TTG AAG GGC CTA ATG CAC GCA CTA AAG CAC TCA     1056
Gly Asp Gln Asp Thr Leu Lys Gly Leu Met His Ala Leu Lys His Ser
            320                 325                 330

AAG ACG TAC CAC TTT CCC AAA ACT GTC ACT CAG AGT CTA AAG AAG ACC     1104
Lys Thr Tyr His Phe Pro Lys Thr Val Thr Gln Ser Leu Lys Lys Thr
                335                 340                 345

ATC AGG TTC CTT CAC AGC TTC ACA ATG TAC AAA TTG TAT CAG AAG TTA     1152
Ile Arg Phe Leu His Ser Phe Thr Met Tyr Lys Leu Tyr Gln Lys Leu
        350                 355                 360

TTT TTA GAA ATG ATA GGT AAT CTA GAA AAG ATC TAA                     1188
Phe Leu Glu Met Ile Gly Asn Leu Glu Lys Ile
365                 370
```

(2) INFORMATION FOR SEQ ID NO:4:

(i) SEQUENCE CHARACTERISTICS:
        (A) LENGTH: 395 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asn Lys Leu Leu Cys Cys Ala Leu Val Phe Leu Asp Ile Ser Ile
-21 -20                 -15                 -10

Lys Trp Thr Thr Gln Glu Thr Phe Pro Pro Lys Tyr Leu His Tyr Asp
 -5              1                   5                  10

Glu Glu Thr Ser His Gln Leu Leu Cys Asp Lys Cys Pro Pro Gly Thr
                15                  20                  25

Tyr Leu Lys Gln His Cys Thr Ala Lys Trp Lys Thr Val Cys Ala Pro
            30                  35                  40

Cys Pro Asp His Tyr Tyr Thr Asp Ser Trp His Thr Ser Asp Glu Cys
        45                  50                  55

Leu Tyr Cys Ser Pro Val Cys Lys Glu Leu Gln Tyr Val Lys Gln Glu
60                  65                  70                  75

Cys Asn Arg Thr His Asn Arg Val Cys Glu Cys Lys Glu Gly Arg Tyr
            80                  85                  90

Leu Glu Ile Glu Phe Cys Leu Lys His Arg Ser Cys Pro Pro Gly Phe
            95                 100                 105

Gly Val Val Gln Ala Gly Thr Pro Glu Arg Asn Thr Val Cys Lys Arg
        110                 115                 120
```

-continued

Cys Pro Asp Gly Phe Phe Ser Asn Glu Thr Ser Ser Lys Ala Pro Cys
         125                 130                 135

Arg Lys His Thr Asn Cys Ser Val Phe Gly Leu Leu Leu Thr Gln Lys
140                 145                 150                 155

Gly Asn Ala Thr His Asp Asn Ile Cys Ser Gly Asn Ser Glu Ser Thr
                    160                 165                 170

Gln Lys Cys Gly Ile Asp Val Thr Leu Cys Glu Glu Ala Phe Phe Arg
                175                 180                 185

Phe Ala Val Pro Thr Lys Phe Thr Pro Asn Trp Leu Ser Val Leu Val
            190                 195                 200

Asp Asn Leu Pro Gly Thr Lys Val Asn Ala Glu Ser Val Glu Arg Ile
205                 210                 215

Lys Arg Gln His Ser Ser Gln Glu Gln Thr Phe Gln Leu Leu Lys Leu
220                 225                 230                 235

Trp Lys His Gln Asn Lys Asp Gln Asp Ile Val Lys Ile Ile Gln
                240                 245                 250

Asp Ile Asp Leu Cys Glu Asn Ser Val Gln Arg His Ile Gly His Ala
                255                 260                 265

Asn Leu Thr Phe Glu Gln Leu Arg Ser Leu Met Glu Ser Leu Pro Gly
                270                 275                 280

Lys Lys Val Gly Ala Glu Asp Ile Glu Lys Thr Ile Lys Ala Cys Lys
285                 290                 295

Pro Ser Asp Gln Ile Leu Lys Leu Leu Ser Leu Trp Arg Ile Lys Asn
300                 305                 310                 315

Gly Asp Gln Asp Thr Leu Lys Gly Leu Met His Ala Leu Lys His Ser
                320                 325                 330

Lys Thr Tyr His Phe Pro Lys Thr Val Thr Gln Ser Leu Lys Lys Thr
                335                 340                 345

Ile Arg Phe Leu His Ser Phe Thr Met Tyr Lys Leu Tyr Gln Lys Leu
                350                 355                 360

Phe Leu Glu Met Ile Gly Asn Leu Glu Lys Ile
365                 370

(2) INFORMATION FOR SEQ ID NO:5:

(i) SEQUENCE CHARACTERISTICS:
        (A) LENGTH: 461 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg

```
                100              105              110
Glu Gln Asn Arg Ile Cys Thr Cys Arg Pro Gly Trp Tyr Cys Ala Leu
            115                  120                  125

Ser Lys Gln Glu Gly Cys Arg Leu Cys Ala Pro Leu Arg Lys Cys Arg
        130                  135                  140

Pro Gly Phe Gly Val Ala Arg Pro Gly Thr Glu Thr Ser Asp Val Val
145                  150                  155                  160

Cys Lys Pro Cys Ala Pro Gly Thr Phe Ser Asn Thr Thr Ser Ser Thr
                165                  170                  175

Asp Ile Cys Arg Pro His Gln Ile Cys Asn Val Val Ala Ile Pro Gly
            180                  185                  190

Asn Ala Ser Met Asp Ala Val Cys Thr Ser Thr Ser Pro Thr Arg Ser
        195                  200                  205

Met Ala Pro Gly Ala Val His Leu Pro Gln Pro Val Ser Thr Arg Ser
210                  215                  220

Gln His Thr Gln Pro Thr Pro Glu Pro Ser Thr Ala Pro Ser Thr Ser
225                  230                  235                  240

Phe Leu Leu Pro Met Gly Pro Ser Pro Ala Glu Gly Ser Thr Gly
                245                  250                  255

Asp Phe Ala Leu Pro Val Gly Leu Ile Val Gly Val Thr Ala Leu Gly
            260                  265                  270

Leu Leu Ile Ile Gly Val Val Asn Cys Val Ile Met Thr Gln Val Lys
        275                  280                  285

Lys Lys Pro Leu Cys Leu Gln Arg Glu Ala Lys Val Pro His Leu Pro
        290                  295                  300

Ala Asp Lys Ala Arg Gly Thr Gln Gly Pro Glu Gln Gln His Leu Leu
305                  310                  315                  320

Ile Thr Ala Pro Ser Ser Ser Ser Ser Leu Glu Ser Ser Ala Ser
                325                  330                  335

Ala Leu Asp Arg Arg Ala Pro Thr Arg Asn Gln Pro Gln Ala Pro Gly
            340                  345                  350

Val Glu Ala Ser Gly Ala Gly Glu Ala Arg Ala Ser Thr Gly Ser Ser
        355                  360                  365

Asp Ser Ser Pro Gly Gly His Gly Thr Gln Val Asn Val Thr Cys Ile
        370                  375                  380

Val Asn Val Cys Ser Ser Ser Asp His Ser Ser Gln Cys Ser Ser Gln
385                  390                  395                  400

Ala Ser Ser Thr Met Gly Asp Thr Asp Ser Ser Pro Ser Glu Ser Pro
                405                  410                  415

Lys Asp Glu Gln Val Pro Phe Ser Lys Glu Glu Cys Ala Phe Arg Ser
            420                  425                  430

Gln Leu Glu Thr Pro Glu Thr Leu Leu Gly Ser Thr Glu Glu Lys Pro
        435                  440                  445

Leu Pro Leu Gly Val Pro Asp Ala Gly Met Lys Pro Ser
        450                  455                  460

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:
```

GCCAGAGGAT CCGAAACGTT TCCTCCAAAG TAC                                33

(2) INFORMATION FOR SEQ ID NO:7:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:7:

CGGCTTCTAG AATTACCTAT CATTTCTAAA AAT                                33

(2) INFORMATION FOR SEQ ID NO:8:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:8:

CGCGGATCCG CCATCATGAA CAAGTTGCTG TG                                 32

(2) INFORMATION FOR SEQ ID NO:9:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:9:

CGCGGTACCC AATTGTGAGG AAACAG                                       26

(2) INFORMATION FOR SEQ ID NO:10:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:10:

GCGCGGATCC ATGAACAAGT TGCTGTGCTG C                                  31

(2) INFORMATION FOR SEQ ID NO:11:

(i) SEQUENCE CHARACTERISTICS:
         (A) LENGTH: 34 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:11:

GCGCTCTAGA TTACCTATCA TTTCTAAAAA TAAC                               34

(2) INFORMATION FOR SEQ ID NO:12:

-continued

```
    (i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:12:

CGCGGATCCG CCATCATGAA CAAGTTGCTG TG                                  32

(2) INFORMATION FOR SEQ ID NO:13:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:13:

CGCGGTACCC AATTGTGAGG AAACAG                                         26

(2) INFORMATION FOR SEQ ID NO:14:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:14:

CGCGGATCCG CCATCATGAA CAAGTTGCTG TG                                  32

(2) INFORMATION FOR SEQ ID NO:15:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:15:

CGCGGTACCC AATTGTGAGG AAACAG                                         26
```

HUMAN TUMOR NECROSIS FACTOR RECEPTOR-LIKE GENES

The present application is a continuation-in-part of U.S. application Ser. No. 08/469,637, filed Jun. 6, 1995 now U.S. Pat. No. 7,094,564, which disclosure is herein incorporated by reference; said Ser. No. 08/469,637 is a continuation-in-part of PCT/US/95/03216, filed Mar. 15, 1995, which disclosure is herein incorporated by reference.

BACKGROUND OF THE INVENTION

1. Field of the Invention

The present inventors have discovered novel receptors in the Tumor Necrosis Factor (TNF) receptor family. In particular, receptors having homology to the type 2 TNF receptor (TNF-RII) are provided. Isolated nucleic acid molecules are also provided encoding the novel receptors of the present invention. Receptor polypeptides are further provided as are vectors, host cells and recombinant methods for producing the same.

2. Related Art

Human tumor necrosis factors α (TNF-α) and β (TNF-β or lymphotoxin) are related members of a broad class of polypeptide mediators, which includes the interferons, interleukins and growth factors, collectively called cytokines (Beutler, B. and Cerami, A., *Annu. Rev. Immunol.*, 7:625-655 (1989)).

Tumor necrosis factor (TNF-α and TNF-β) was originally discovered as a result of its anti-tumor activity, however, now it is recognized as a pleiotropic cytokine playing important roles in a host of biological processes and pathologies. To date, there are ten known members of the TNF-related cytokine family, TNF-α, TNF-β (lymphotoxin-α), LT-β, TRAIL and ligands for the Fas receptor, CD30, CD27, CD40, OX40 and 4-1BB receptors. These proteins have conserved C-terminal sequences and variable N-terminal sequences which are often used as membrane anchors, with the exception of TNF-β. Both TNF-α and TNF-β function as homotrimers when they bind to TNF receptors.

TNF is produced by a number of cell types, including monocytes, fibroblasts, T-cells, natural killer (NK) cells and predominately by activated macrophages. TNF-α has been reported to have a role in the rapid necrosis of tumors, immunostimulation, autoimmune disease, graft rejection, producing an anti-viral response, septic shock, cerebral malaria, cytotoxicity, protection against deleterious effects of ionizing radiation produced during a course of chemotherapy, such as denaturation of enzymes, lipid peroxidation and DNA damage (Nata et al., *J. Immunol.* 136(7):2483 (1987)), growth regulation, vascular endothelium effects and metabolic effects. TNF-α also triggers endothelial cells to secrete various factors, including PAI-1, IL-1, GM-CSF and IL-6 to promote cell proliferation. In addition, TNF-α up-regulates various cell adhesion molecules such as E-Selectin, ICAM-1 and VCAM-1. TNF-α and the Fas ligand have also been shown to induce programmed cell death.

TNF-β has many activities, including induction of an antiviral state and tumor necrosis, activation of polymorphonuclear leukocytes, induction of class I major histocompatibility complex antigens on endothelial cells, induction of adhesion molecules on endothelium and growth hormone stimulation (Ruddle, N. and Horner, R., *Prog. Allergy*, 40:162-182 (1988)).

Recent studies with "knockout" mice have shown that mice deficient in TNF-β production show abnormal development of the peripheral lymphoid organs and morphological changes in spleen architecture (reviewed in Aggarwal et al., *Eur Cytokine Netw*, 7(2):93-124 (1996)). With respect to the lymphoid organs, the popliteal, inguinal, para-aortic, mesenteric, axillary and cervical lymph nodes failed to develop in TNF-β−/− mice. In addition, peripheral blood from TNF-β−/− mice contained a three fold reduction in white blood cells as compared to normal mice. Peripheral blood from TNF-β−/− mice, however, contained four fold more B cells as compared to their normal counterparts. Further, TNF-β, in contrast to TNF-α has been shown to induce proliferation of EBV-infected B cells. These results indicate that TNF-β is involved in lymphocyte development.

The first step in the induction of the various cellular responses mediated by TNF or LT is their binding to specific cell surface or soluble receptors. Two distinct TNF receptors of approximately 55-KDa (TNF-RI) and 75-KDa (TNF-RII) have been identified (Hohman et al., *J. Biol. Chem.*, 264: 14927-14934 (1989)), and human and mouse cDNAs corresponding to both receptor types have been isolated and characterized (Loetscher et al., *Cell*, 61:351 (1990)). Both TNF-Rs share the typical structure of cell surface receptors including extracellular, transmembrane and intracellular regions.

These molecules exist not only in cell bound forms, but also in soluble forms, consisting of the cleaved extra-cellular domains of the intact receptors (Nophar et al., *EMBO Journal*, 9 (10):3269-76 (1990)) and otherwise intact receptors wherein the transmembrane domain is lacking. The extracellular domains of TNF-RI and TNF-RII share 28% identity and are characterized by four repeated cysteine-rich motifs with significant intersubunit sequence homology. The majority of cell types and tissues appear to express both TNF receptors and both receptors are active in signal transduction, however, they are able to mediate distinct cellular responses. Further, TNF-RII was shown to exclusively mediate human T-cell proliferation by TNF as shown in PCT WO 94/09137.

TNF-RI dependent responses include accumulation of C-FOS, IL-6, and manganese superoxide dismutase mRNA, prostaglandin E2 synthesis, IL-2 receptor and MHC class I and II cell surface antigen expression, growth inhibition, and cytotoxicity. TNF-RI also triggers second messenger systems such as phospholipase $A_2$, protein kin se C phosphatidylcholine-specific phospholipase C and sphingomyelinase (Pfeffer, K., et al., *Celt*, 73:457-467 (1993)).

Several interferons and other agents have been shown to regulate the expression of TNF-Rs. Retinoic acid, for example, has been shown to induce the production of TNF receptors in some cells type while down regulating production in other cells. In addition, TNF-α has been shown effect the localization of both types of receptor. TNF-α induces internalization of TNF-RI and secretion of TNF-RII (reviewed in Aggarwal et al., supra). Thus, the production and localization of both TNF-Rs are regulated by a variety of agents.

The yeast two hybrid system has been used to identify ligands which associate with both types of the TNF-Rs (reviewed in Aggarwal et al., supra). Several proteins have been identified which interact with the cytoplasmic domain of a murine TNF-R. Two of these proteins appear to be related to the baculovirus inhibitor of apoptosis, suggesting a direct role for TNF-R in the regulation of programmed cell death.

SUMMARY OF THE INVENTION

The novel Tumor Necrosis Factor (TNF) family receptors of the present invention are referred to herein as "TR1 receptors". Thus, in accordance with one aspect of the present invention, there are provided isolated nucleic acid molecules encoding the TR1 polypeptides of the present invention, including mRNAs, DNAs, cDNAs, genomic DNA as well as antisense analogs thereof and biologically active and diagnostically or therapeutically useful fragments thereof. These isolated nucleic acid molecules include polynucleotide molecules encoding the native TR1 receptor polypeptide having the amino acid sequence shown in FIG. 1 (SEQ ID NO:2) or the amino acid sequence encoded by the cDNA clone deposited in a bacterial host as ATCC Deposit Number 75899 on Sep. 28, 1994. The nucleotide sequence determined by sequencing the deposited native TR1 receptor clone, which is shown in FIG. 1 (SEQ ID NO:1), contains an open reading frame encoding a polypeptide of 401 amino acid residues, including an initiation codon at positions 46-48 in FIG. 1, with a leader sequence of about 21 amino acid residues, and a predicted molecular weight of about 46 kDa for the whole protein and about 44 kDa for the non-glycosylated mature protein. The amino acid sequence of the predicted mature native TR1 receptor protein is shown in FIG. 1, amino acid residues about 22 to about 401 (SEQ ID NO:2).

Also included in the present invention are isolated nucleic acid molecules encoding a carboxy terminus modified TR1 receptor polypeptide having the amino acid sequence shown in FIG. 2 (SEQ ID NO:4). The nucleotide sequence encoding a carboxy terminus modified TR1 receptor polypeptide, shown in FIG. 2 (SEQ ID NO:3), contains an open reading frame encoding a polypeptide of 395 amino acid residues, including an initiation codon at positions 1-3 in FIG. 2, with a leader sequence of about 21 amino acid residues, and a predicted molecular weight of about 43 kDa for the non-glycosylated mature protein. The amino acid sequence of the mature carboxy terminus modified TR1 receptor protein is shown in FIG. 2, amino acid residues from about 22 to about 395 (SEQ ID NO:4).

In a further aspect the invention provides an isolated nucleic acid molecule comprising a polynucleotide having a nucleotide sequence selected from the group consisting of: (a) a nucleotide sequence encoding a TR1 receptor polypeptide having the complete amino acid sequence in FIG. 1 (SEQ ID NO:2) or FIG. 2 (SEQ ID NO:4); (b) a nucleotide sequence encoding the predicted mature native TR1 receptor polypeptide having the amino acid sequence at about position 22 to about position 401 in FIG. 1 (SEQ ID NO:2) or the predicted mature carboxy terminus modified TR1 receptor polypeptide having the amino acid sequence at about position 22 to about position 395 in FIG. 2 (SEQ ID NO:4); (c) a nucleotide sequence encoding the native TR1 receptor polypeptide having the complete amino acid sequence encoded by the cDNA clone contained in ATCC Deposit No. 75899; (d) a nucleotide sequence encoding the mature native TR1 receptor polypeptide having the amino acid sequence encoded by the cDNA clone contained in ATCC Deposit No. 75899; and (e) a nucleotide sequence complementary to any of the nucleotide sequences in (a), (b), (c) or (d) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d) or (e), above, or a polynucleotide which hybridizes under stringent hybridization conditions to a polynucleotide in (a), (b), (c), (d) or (e), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a TR1 receptor polypeptide having an amino acid sequence in (a), (b), (c) or (d), above.

In accordance with another aspect of the present invention, there are provided novel mature polypeptides which are TR1 receptors, as well as fragments, analogs and derivatives thereof. The polypeptides of the present invention are of human origin and have amino acid sequences selected from the group consisting of: (a) the amino acid sequence of the native TR1 receptor polypeptide having the complete 401 amino acid sequence, including the leader sequence, shown in FIG. 1 (SEQ ID NO:2), or the amino acid sequence of the carboxy terminus modified TR1 receptor polypeptide having the complete 395 amino acid sequence, including the leader sequence, shown in FIG. 2 (SEQ ID NO:4); (b) the amino acid sequence of the predicted mature native TR1 receptor polypeptide (without the leader) having the amino acid sequence at about position 22 to about position 401 in FIG. 1 (SEQ ID NO:2) or the amino acid sequence of the predicted mature carboxy terminus modified TR1 receptor polypeptide (without the leader) having the amino acid sequence at about position 22 to about position 395 in FIG. 2 (SEQ ID NO:4); (c) the amino acid sequence of the native TR1 receptor polypeptide having the complete amino acid sequence, including the leader, encoded by the cDNA clone contained in ATCC Deposit No. 75899; and (d) the amino acid sequence of the mature native TR1 receptor polypeptide having the amino acid sequence encoded by the cDNA clone contained in ATCC Deposit No. 75899. The polypeptides of the present invention also include polypeptides having an amino acid sequence with at least 90% similarity, and more preferably at least 95% similarity to those described in (a), (b), (c) or (d) above, as well as polypeptides having an amino acid sequence at least 80% identical, more preferably at least 90% identical, and still more preferably 95%, 96%, 97%, 98% or 99% identical to those above.

The above-described soluble TR1 receptor polypeptides are believed not to include amino acids comprising a transmembrane domain. Thus, in a further aspect, the present invention provides TR1 receptor polypeptides that include such a transmembrane domain-containing amino acid sequence. Such polypeptides may be native or constructed from the TR1 receptors described herein.

An additional embodiment of this aspect of the invention relates to a peptide or polypeptide which has the amino acid sequence of an epitope-bearing portion of a TR1 receptor polypeptide having an amino acid sequence described in (a), (b), (c) or (d), above. Peptides or polypeptides having the amino acid sequence of an epitope-bearing portion of a TR1 receptor polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention. In another embodiment, the invention provides an isolated antibody that binds specifically to a TR1 receptor polypeptide having an amino acid sequence described in (a), (b), (c) or (d) above.

The invention also provides functional domains of the soluble TR1 receptor polypeptides of the present invention. These domains include amino acid residues from about 22 to about 261 in FIG. 1 (SEQ ID NO:2) and FIG. 2 (SEQ ID NO:4). The inventors have discovered that amino acid residues from about 22 to about 261 in FIGS. 1 and 2 are homologous to the extracellular domain of a publicly known TNF- RII (FIG. 3). Further included are amino acid residues from about 262 to about 401 in FIG. 1 (SEQ ID NO:2) and amino acid residues from about 262 to about 395 in FIG. 2 (SEQ ID NO:4), which the present inventors have discovered are homologous to the intracellular domain of the publicly known TNF-RII (FIG. 3).

The invention further provides methods for isolating antibodies that bind specifically to a TR1 receptor polypeptide having an amino acid sequence as described herein. Such antibodies are useful diagnostically or therapeutically as described below.

In accordance with yet a further aspect of the present invention, there is provided a process for producing such polypeptides by recombinant techniques which comprises culturing recombinant prokaryotic and/or eukaryotic host cells, containing a nucleic acid sequence encoding a polypeptide of the present invention, under conditions promoting expression of said protein and subsequent recovery of said protein. Thus, the present invention also relates to methods of making such vectors and host cells and for using them for production of TR1 receptor polypeptides or peptides by recombinant techniques.

In accordance with yet a further aspect of the present invention, there is provided a process for utilizing such polypeptides, or polynucleotide encoding such polypeptides to screen for receptor antagonists and/or agonists and/or receptor ligands. Such a screening method for identifying compounds capable of enhancing or inhibiting a cellular response induced by the TR1 receptor involves contacting cells which express the TR1 receptor with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

In accordance with yet a further aspect of the present invention, there are provided nucleic acid probes comprising nucleic acid molecules of sufficient length to specifically hybridize to the polypeptide of the present invention.

In another aspect, screening assays for agonists and antagonists are provided which involve determining the effect a candidate compound has on the binding of cellular ligands capable of either eliciting or inhibiting a TR1 receptor mediated response. In particular, the methods involve contacting a TR1 receptor polypeptide with a candidate compound and determining whether TR1 receptor polypeptide binding to the cellular ligand is increased or decreased due to the presence of the candidate compound. Further, if binding to the TR1 receptor by the cellular ligand is altered, the effect on TR1 receptor activity is then determined. In addition, such assays may be used to identify compound which directly elicit a TR1 receptor mediated response.

In accordance with still another aspect of the present invention, there is provided a process of using such agonists for treating conditions related to insufficient TR1 receptor activity, for example, to inhibit tumor growth, to stimulate human cellular proliferation, e.g., T-cell proliferation, to regulate the immune response and antiviral responses, to protect against the effects of ionizing radiation, to protect against chlamidiae infection, to regulate growth and to treat immunodeficiencies such as is found in HIV.

In accordance with another aspect of the present invention, there is provided a process of using such antagonists for treating conditions associated with over-expression of the TR1 receptor, for example, for treating T-cell mediated autoimmune diseases such as AIDS, septic shock, cerebral malaria, graft rejection, cytotoxicity, cachexia, apoptosis and inflammation.

The present inventors have discovered that TR1 receptor is expressed in pulmonary tissue, hippocampus, adult heart, kidney, liver, placenta, smooth muscle, thymus, prostate, ovary, small intestine and osteoblastoma and fibroblast cell lines. Further, the inventors have shown that a detectable quantity of TR1 receptor mRNA is not present in fetal brain, synovium, synovial sarcoma, T-cells, endothlial cells, activated macrophages, lymph nodes, thymus, neutrophils, and activated neutrophils. For a number of disorders, it is believed that significantly higher or lower levels of one or both of the TR1 receptor gene expressions can be detected in certain tissues (e.g., cancer, apoptosis and inflammation) or bodily fluids (e.g., serum, plasma, urine, synovial fluid or spinal fluid) taken from an individual having such a disorder, relative to a "standard" TR1 receptor gene expression level, i.e., the TR1 receptor expression level in tissue or bodily fluids from an individual not having one of the disorders associated with aberrant TR1 receptor function. Thus, the invention provides a diagnostic method useful during diagnosis of a disorder associated with aberrant TR1 receptor function, which involves: (a) assaying TR1 receptor gene expression level in cells or body fluid of an individual; (b) comparing the TR1 receptor gene expression level with a standard TR1 receptor gene expression level, whereby an increase or decrease in the assayed TR1 receptor gene expression level compared to the standard expression level is indicative of a disorder associated with aberrant TR1 receptor function.

BRIEF DESCRIPTION OF THE FIGURES

FIG. 1(A-B) shows the cDNA sequence (SEQ ID NO:1) and corresponding deduced amino acid sequence (SEQ ID NO:2) of the native TR1 receptor polypeptide of the present invention which is believed to lack a transmembrane domain. The initial 21 amino acids represent the putative leader sequence and are underlined. The standard one-letter abbreviations for amino acids are used. Sequencing was performed using a 373 automated DNA sequencer (Applied Biosystems, Inc.). Sequencing accuracy is predicted to be greater than 97% accurate.

FIG. 2(A-B) shows the cDNA sequence (SEQ ID NO:3) and corresponding deduced amino acid sequence (SEQ ID NO:4) of the carboxy terminus modified TR1 receptor polypeptide of the present invention. As above, underlined. Sequencing and abbreviations are as in FIG. 1.

FIG. 3 illustrates an amino acid sequence alignment of the native TR1 receptor polypeptide of the present invention (upper line) and the publically known human type 2 TNF receptor (human TNF-RII, shown on the lower line).

FIG. 9 shows a screening assay (ELISA) of polyclonal rabbit anti-TR1 antibodies. Polyclonal rabbit anti-TR1 antibodies were prepared by Pocono Rabbit Farm & Laboratory, Inc. (Canadensis, Pa. 18325) according standard protocol. The rabbit serum was tested by ELISA. In particular, the plates were coated with TR1 (labeled as TNFr batch HG02900-1-B) for 2 hr at room temperature or overnight at 4° C. After washing with PBS, they were blocked with PBS with 1% BSA and 0.5% sodium azide at 4° C. overnight. The PBS-BSA was flicked out of the well and test supernatants were added and incubated for 1 hr at room temperature. After 3 washes with PBS, 50 ml of anti-rabbit IgG horseradish peroxidase conjugate (1:1000 dilution in PBS with 1% BSA) was added and incubated at room temperature for 0.5-1 hr. After 3 washes with PBS, the substrate solution for IgG horseradish peroxidase was added to the plate and incubated at room temperature for 10-30 min. The reaction was stopped by adding 50 ml of 0.1 M EDTA. The absorbance was read at 450 nm.

DETAILED DESCRIPTION OF THE PREFERRED EMBODIMENTS

Nucleic Acid Molecules

Figure 4:
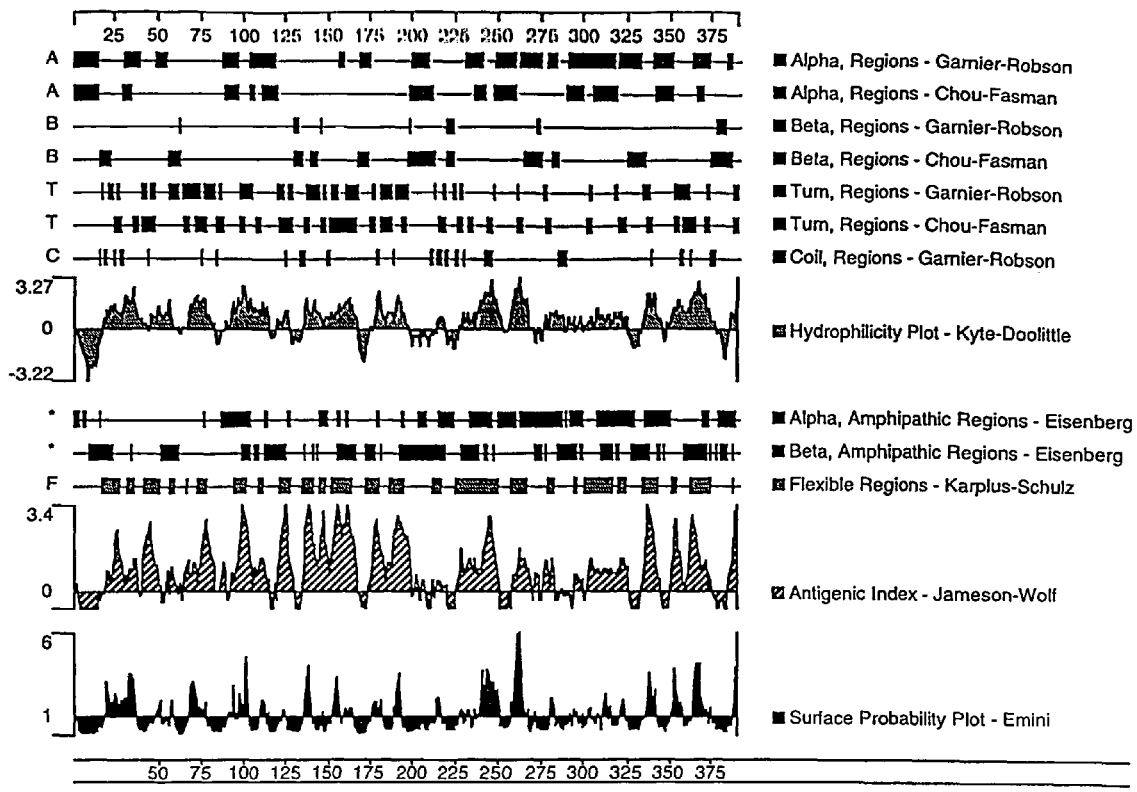
FIG. 4 shows an analysis of the native TR1 receptor amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues 20-52, 66-203, 229-279, 297-378 in FIG. 1 correspond to the shown highly antigenic regions of the native TR1 receptor protein.
Figure 5:
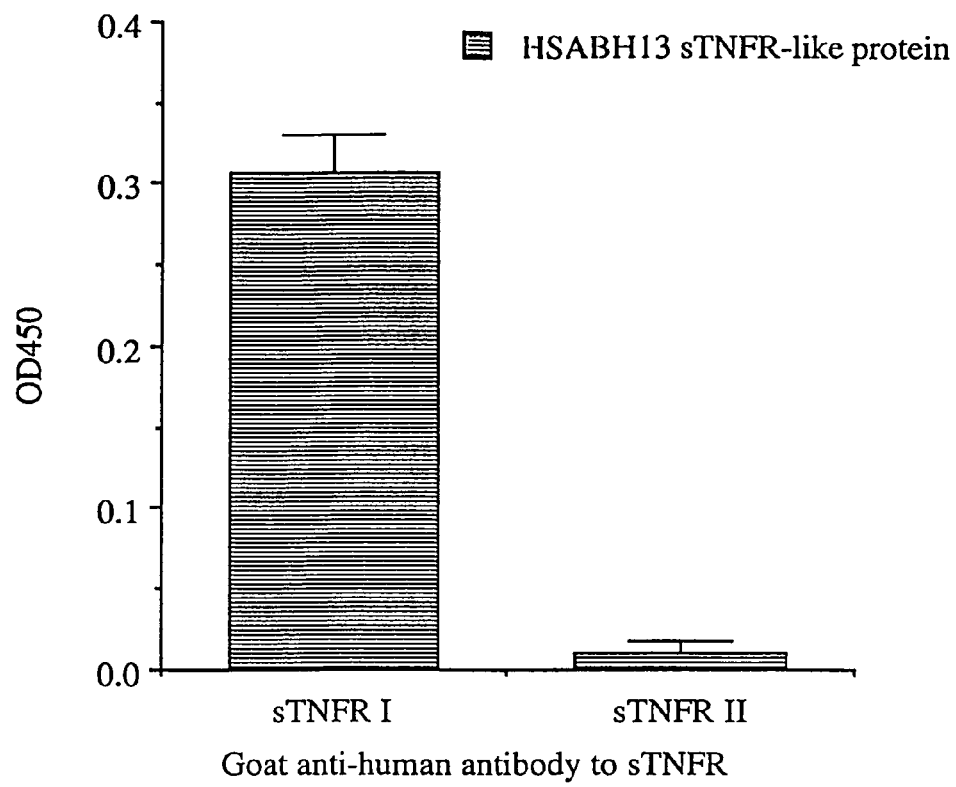
FIG. 5 shows a binding assay of polyclonal antibodies specific for human TNF-RI and TNF-RII and the native TR1 receptor of the present invention. Purified native TR1 receptor (HSABH13 protein) was added to well in a 96-well plate (100 µl/well), and incubated for 2 hr. After incubation, the plate was washed three times and phosphatase-labeled goat polyclonal antibody to human TNF-RI and TNF-RII (200 µl) was added to each well. After a further 2 hr incubation the receptor-antibody conjugate was washed three times and 200 µl of substrate solution was added to each well. The plate was incubated further for 1 hr. The O.D. of the resulting solution was then measured using a ELISA reader (test wavelength 450 nm, correction wavelength 590 nm). All reagents were from R & D System (Minneapolis, Minn. 55413) and were used according to the manufacturer's instructions.
Figure 6:
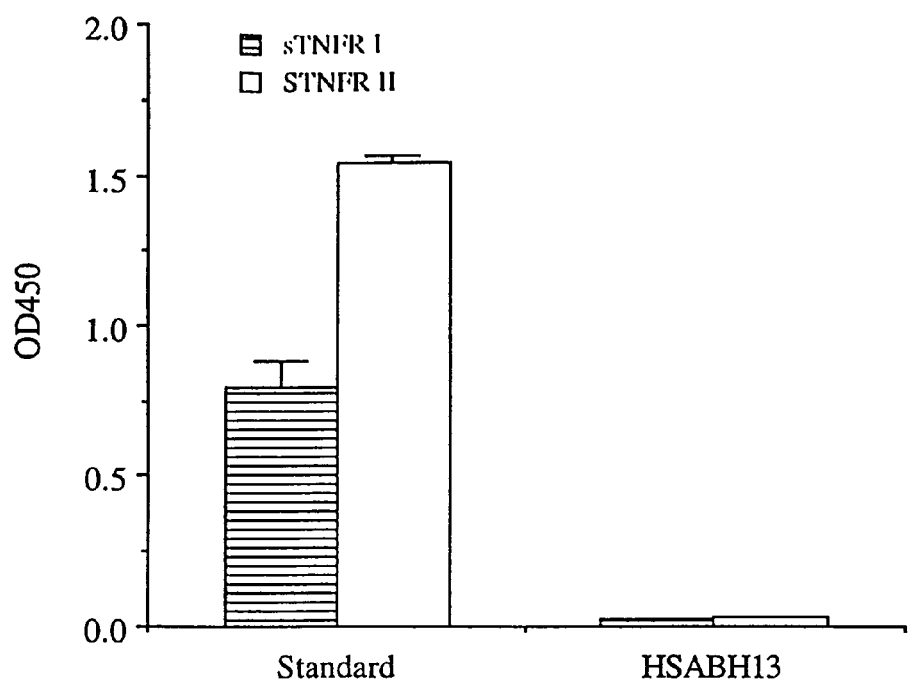
FIG. 6 shows a binding assay of the native TR1 receptor to monoclonal antibodies specific for type I and II TNF receptors. Purified native TR1 receptor (HSABH13 protein) (100 ul/well) was added to a 96-well plate provided by R&D system which was coated with mAbs to sTNFRI or sTNFRII, and incubated for 2 hr. After washing three times with washing buffer, phosphatase-labeled polyclonal antibody to sTNF RI or sTNF RII (200 ml) was added. After 2 hr incubation and three times wash, 200 ml of substrate solution was added to each well and the plate was incubated for 1 hr. The OD was measured using a ELISA reader (test wavelength 450 nm, correction wavelength 590 nm). All reagents were from R & D System.

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U.

The term "gene" or "cistron" means the segment of DNA involved in producing a polypeptide chain; it includes regions preceding and following the coding region (leader and trailer) as well as intervening sequences (introns) between individual coding segments (exons).

In accordance with an aspect of the present invention, there is provided an isolated nucleic acid (polynucleotide) which encodes the predicted mature native TR1 receptor polypeptide having the deduced amino acid sequence of FIG. 1 (SEQ ID NO:2) or for the mature native TR1 receptor polypeptide encoded by the cDNA of the clone which was deposited on Sep. 28, 1994 at the American Type Culture Collection Patent Depository, 10801 University Boulevard, Manassas, Va. 20110-2209, and given accession number 75899. The nucleotide sequence shown in FIG. 1 (SEQ ID NO:1) was obtained by sequencing the HSABH13 clone deposited with the ATCC. The deposited clone is contained in the pBluescript SK(–) plasmid (Stratagene, LaJolla, Calif.).

Also provided is an isolated nucleic acid (polynucleotide) which encodes the mature carboxy terminus modified TR1 receptor polypeptide having the deduced amino acid sequence of FIG. 2 (SEQ ID NO:4), which includes a frame shift at a carboxy terminal amino acid residue shown in FIG. 1 (SEQ ID NO:2). Due to the location of this frame shift, the inventors, as one skilled in the art would recognize, predict that a functional TR1 receptor with a modified carboxy terminus is encoded by FIG. 2 (SEQ ID NO:3). This conclusion is based on the fact that the remainder of the sequence remains substantially unaltered.

One skilled in the art would be able to produce such a carboxy terminus modified TR1 receptor as shown in FIG. 2 (SEQ ID NO:4) from the cDNA clone contained in ATCC Deposit No. 75899 or from an isolated naturally occurring polynucleotide using standard recombinant DNA techniques, which are described in numerous sources including in *Molecular Cloning, A Laboratory Manual,* 2nd. edition, Sambrook, J., Fritsch, E. F. and Maniatis, T., eds., Cold Spring Harbor Laboratory Press, Cold Spring Harbor, N.Y. (1989).

Using the information provided herein, such as the nucleotide sequence in FIG. 1 (SEQ ID NO:1) or FIG. 2 (SEQ ID NO:3), a cDNA molecule comprising a polynucleotide encoding a polypeptide of the present invention may be obtained from numerous human tissues, including pulmonary tissue, hippocampus, adult heart, kidney, liver, placenta, smooth muscle, thymus, prostate, ovary, small intestinal tissue and osteoblastoma and fibroblast cell lines. The present inventors have discovered that the native TR1 receptor of the present invention is expressed in each of the above tissues and cell types.

The cDNA clone contained in ATCC Deposit No. 75899 was isolated from a cDNA library derived from human early passage fibroblasts (HSA 172 cells) and is structurally related to a prior art human TNF-RII receptor. See FIG. 3 (SEQ ID NO:5). The determined nucleotide sequence of the TR1 receptor cDNA of FIG. 1 (SEQ ID NO:1) contains an initiation codon at positions 46-48 of the nucleotide sequence in FIG. 1 (SEQ ID NO:1) and contains an open reading frame encoding a protein of 401 amino acid residues of which approximately the first 21 amino acids residues are the putative leader sequence such that the mature protein comprises about 380 amino acids. The protein exhibits the highest degree of homology to human TNF-R2 with about 27% identity and about 43% similarity over the entire length of the proteins. Six conserved cyteines present in modules of 40 residues in all TNF receptors are conserved in this receptor.

As indicated, the present invention also provides the mature form(s) of the TR1 receptor proteins of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature TR1 receptor polypeptides having the amino acid sequence encoded by the cDNA clone contained in the host identified as ATCC Deposit No. 75899 and as shown in FIG. 1 (SEQ ID NO:2) and FIG. 2 (SEQ ID NO:4). By the mature TR1 receptor having the amino acid sequence encoded by the cDNA clone contained in the host identified as ATCC Deposit No. 75899 is meant the mature form(s) of the TR1 receptor protein produced by expression in a mammalian cell (e.g., COS cells, as described below) of the complete open reading frame encoded by the human DNA sequence of the clone contained in the vector in the deposited host. As indicated below, the mature TR1 receptor having the amino acid sequence encoded by the cDNA clone contained in ATCC Deposit No. 75899 may or may not differ from the predicted "mature" TR1 receptor protein shown in FIG. 1 (amino acids from about 22 to about 401) depending on the accuracy of the predicted cleavage site based on computer analysis.

Methods for predicting whether a protein has a secretory leader as well as the cleavage point for that leader sequence are available because it is known that much of the cleavage specificity for a secretory protein resides in certain amino acid residues within the signal sequence and the N-terminus of the mature protein, particularly residues immediately surrounding the cleavage site. For instance, the method of McGeoch (*Virus Res.* 3:271-286 (1985)) uses the information from a short N-terminal charged region and a subsequent uncharged region of the complete (uncleaved) protein. The method of von Heinje (*Nucleic Acids Res.* 14:4683-4690 (1986)) uses the information from the residues surrounding the cleavage site, typically residues –13 to +2 where +1 indicates the amino acid terminus of the mature protein. The accuracy of predicting the cleavage points of known mammalian secretory proteins for each of these methods is in the range of 75-80%. von Heinje, supra. However, the two methods do not always produce the same predicted cleavage point(s) for a given protein.

In the present case, the predicted amino acid sequence of the complete TR1 receptor polypeptides of the present invention were analyzed by a computer program ("PSORT"). This program is available from Dr. Kenta Nakai of the Institute for Chemical Research, Kyoto University (see K. Nakai and M. Kanehisa, *Genomics* 14:897-911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage sites between amino acids 21 and 22 in FIG. 1 (SEQ ID NO:2) and FIG. 2 (SEQ ID NO:4). Thereafter, the complete amino acid sequences were further analyzed by visual inspection, applying a simple form of the (–1,–3) rule of von Heine. von Heinje, supra. Thus, the leader sequence for the native TR1 receptor protein is predicted to consist of amino acid residues 1-21 in FIG. 1 (SEQ ID NO:2), while the predicted mature native TR1 receptor protein consists of residues 22-401, and the leader sequence for the carboxy terminus modified TR1 receptor protein is predicted to consist of amino acid residues 1-21 in FIG. 2 (SEQ ID NO:4), while the predicted mature native TR1 receptor protein consists of residues 22-395 in FIG. 2 (SEQ ID NO:4).

Thus, in view of above, as one of ordinary skill would appreciate, the actual leader sequence of the TR1 receptor proteins of the present invention are predicted to be about 21 amino acids in length, but may be anywhere in the range of about 16 to about 27 amino acids. The TR1 receptors of the present invention are soluble receptors and are secreted. However, they may also exist as membrane bound receptors having a transmembrane region and intra- and extracellular regions. The polypeptides of the present invention may bind TNF and lymphotoxin ligands or other TNF ligand family members.

In accordance with an aspect of the present invention there are provided polynucleotides which may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1), FIG. 2 (SEQ ID NO:3) or that of the deposited clone or may be a different coding sequence which coding sequence, as a result of the redundancy or degeneracy of the genetic code, encodes the same mature polypeptide as the DNA of FIG. 1 (SEQ ID NO:1), FIG. 2 (SEQ ID NO:3) or the deposited cDNA.

The polynucleotide which encodes for the mature polypeptide of FIG. 1 (SEQ ID NO:2), FIG. 2 (SEQ ID NO:4) or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode fragments, analogs and derivatives of the polypeptide having the deduced amino acid sequence of FIG. 1 (SEQ ID NO:2), FIG. 2 (SEQ ID NO:4), or the polypeptide encoded by the cDNA of the deposited clone. The variant of the polynucleotides may be naturally occurring allelic variant of the polynucleotide or non-naturally occurring variants of those polynucleotides.

By a fragment of an isolated nucleic acid molecule having the nucleotide sequence of the deposited cDNA or the nucleotide sequence shown in FIG. 1 (SEQ ID NO:1) or FIG. 2 (SEQ ID NO:4) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50-1000 nt in length are also useful according to the present invention as are fragments corresponding to most, if not all, of the nucleotide sequence shown in FIG. 1 (SEQ ID NO:1), FIG. 2 (SEQ ID NO:3), of the deposited cDNA. By a fragment at least 20 nt in length, for example, is intended fragments which include 20 or more contiguous bases from the nucleotide sequence of the deposited cDNA or the nucleotide sequence as shown in FIG. 1 (SEQ ID NO:1) or FIG. 2 (SEQ ID NO:3). Since the gene has been deposited and the nucleotide sequence shown in FIG. 1 (SEQ ID NO:1) and FIG. 2 (SEQ ID NO:3) are provided, generating such DNA fragments would be routine to the skilled artisan. For example, restriction endonuclease cleavage or shearing by sonication could easily be used to generate fragments of various sizes. Alternatively, such fragments could be generated synthetically.

Preferred nucleic acid fragments of the present invention include nucleic acid molecules encoding epitope-bearing portions of the TR1 receptor protein. In particular, such nucleic acid fragments of the present invention include nucleic acid molecules encoding: a polypeptide comprising amino acid residues from about 20 to about 52 in FIG. 1 (SEQ ID NO:2) or FIG. 2 (SEQ ID NO:4); a polypeptide comprising amino acid residues from about 66 to about 203 in FIG. 1 (SEQ ID NO:2) or FIG. 2 (SEQ ID NO:4); a polypeptide comprising amino acid residues from about 229 to about 279 in FIG. 1 (SEQ ID NO:2) or FIG. 2 (SEQ ID NO:4); and a polypeptide comprising amino acid residues from about 297 to about 378 in FIG. 1 (SEQ ID NO:2). Using the Jameson-Wolf graph shown in FIG. 4, the inventors have determined that the above polypeptide fragments are antigenic regions of the TR1 receptor protein.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1), FIG. 2 (SEQ ID NO:3), or of the coding sequence of the deposited clone. As indicated, one particularly preferred variant is a TR1 receptor containing a transmembrane domain inserted after amino acid residue about 260 or 261 in FIG. 1 or FIG. 2. As known in the art, an allelic variant is an alternate form of a polynucleotide sequence which may have a substitution, deletion or addition of one or more nucleotides, which does not substantially alter the function of the encoded polypeptide. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the TR1 receptor proteins or portions thereof. Also especially preferred in this regard are conservative substitutions. Most highly preferred are nucleic acid molecules encoding the mature native TR1 receptor protein having the amino acid sequence shown in FIG. 1 (SEQ ID NO:2), the mature native TR1 receptor amino acid sequence encoded by the deposited cDNA clone, or the mature carboxy terminus modified TR1 receptor protein having the amino acid sequence shown in FIG. 2 (SEQ ID NO:4).

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains. Such isolated molecules, particularly DNA molecules, are useful as probes for gene mapping, by in situ hybridization with chromosomes, and for detecting expression of the TR1 receptor genes in human tissue, for instance, by Northern blot analysis.

Thus, for example, the polynucleotide of the present invention may encode for a mature protein, or for a protein having a prosequence or for a protein having both a prosequence and a presequence (leader sequence).

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson et al., *Cell,* 37:767 (1984)). The coding sequence may also be fused to a sequence which codes for a fusion protein such as an IgG Fc fusion protein.

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 80%, preferably at least 90%, and more preferably at least 95%, 96%, 97%, 98% or 99% identity between the sequences. The present invention particularly relates to polynucleotides which hybridize under stringent conditions to the hereinabove-described polynucleotides, for instance, the cDNA clone contained in ATCC Deposit 75899. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Of course, polynucleotides hybridizing to a larger portion of the reference polynucleotide (e.g., the deposited cDNA clone), for instance, a portion 50-750 nt in length, or even to the entire length of the reference polynucleotide, are also useful as probes according to the present invention, as are polynucleotides corresponding to most, if not all, of the nucleotide sequence of the deposited cDNA or the nucleotide sequence as shown in FIG. 1 (SEQ ID NO:1) or FIG. 2 (SEQ ID NO:3). By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIG. 1 (SEQ ID NO:1) or FIG. 2 (SEQ ID NO:3)). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual,* 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference.

Since a TR1 receptor cDNA clone has been deposited and its determined nucleotide sequence is provided in FIG. 1 (SEQ ID NO:1), generating polynucleotides which hybridize to a portion of the TR1 receptor cDNA molecule would be routine to the skilled artisan. For example, restriction endonuclease cleavage or shearing by sonication of the TR1 receptor cDNA clone could easily be used to generate DNA portions of various sizes which are polynucleotides that hybridize to a portion of the TR1 receptor cDNA molecule. Alternatively, the hybridizing polynucleotides of the present invention could be generated synthetically according to known techniques. Of course, a polynucleotide which hybridizes only to a poly A sequence (such as the 3' terminal poly(A) tract of the TR1 receptor cDNA shown in FIG. 1 (SEQ ID NO:1), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

Further embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding the full-length native TR1 receptor polypeptide having the complete amino acid sequence in FIG. 1 (SEQ ID NO:2) or a nucleotide sequence encoding the full-length carboxy terminus modified TR1 receptor polypeptide having the complete amino acid sequence in FIG. 2 (SEQ ID NO:4), including the predicted leader sequences; (b) a nucleotide sequence encoding the mature native TR1 receptor polypeptide (full-length polypeptide with the leader removed) having the amino acid sequence at positions about 22 to about 401 in FIG. 1 (SEQ ID NO:2) or a nucleotide sequence encoding the mature carboxy terminus modified TR1 receptor polypeptide (full-length polypeptide with the leader removed) having the amino acid sequence at positions about 22 to about 395 in FIG. 2 (SEQ ID NO:4); (c) a nucleotide sequence encoding the full-length native TR1 receptor polypeptide having the complete amino acid sequence including the leader encoded by the cDNA clone contained in ATCC Deposit No. 75899; (d) a nucleotide sequence encoding the mature native TR1 receptor polypeptide having the amino acid sequence encoded by the cDNA clone contained in ATCC Deposit No. 75899; or (e) a nucleotide sequence complementary to any of the nucleotide sequences in (a), (b), (c) or (d).

By a polynucleotide having a nucleotide sequence at least, for example, 95% "identical" to a reference nucleotide sequence encoding a TR1 receptor polypeptide is intended that the nucleotide sequence of the polynucleotide is identical to the reference sequence except that the polynucleotide sequence may include up to five point mutations per each 100 nucleotides of the reference nucleotide sequence encoding the TR1 receptor polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIG. 1, FIG. 2 or to the nucleotide sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIG. 1 (SEQ ID NO:1), or FIG. 2 (SEQ ID NO:3), or to the nucleic acid sequence of the deposited cDNA, irrespective of whether they encode a polypeptide having TR1 receptor activity. This is because even where a particular nucleic acid molecule does not encode a polypeptide having TR1 receptor activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TR1 receptor activity include, inter alia, (1) isolating the TR1 receptor gene or allelic variants thereof in a cDNA library; (2) in situ hybridization (e.g., "FISH") to metaphase chromosomal spreads to provide precise chromosomal location of the TR1 receptor gene, as described in Verma et al., *Human Chromosomes: A Manual of Basic Techniques*, Pergamon Press, New York (1988); and Northern Blot analysis for detecting TR1 receptor mRNA expression in specific tissues.

Figure 7:
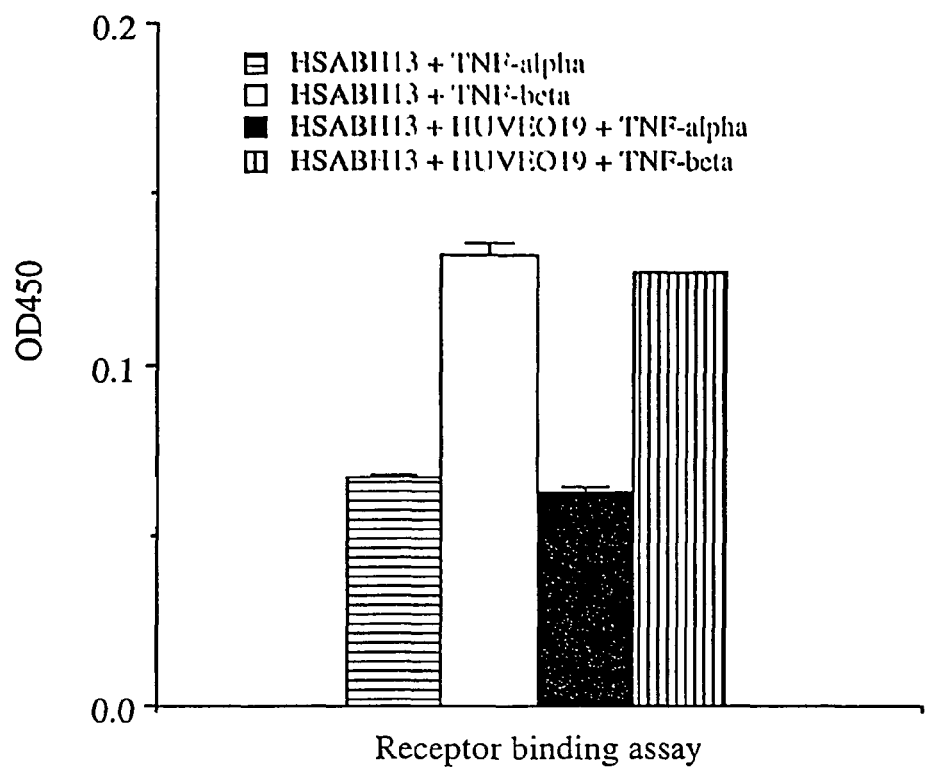
FIG. 7 shows a competitive binding assay between the native TR1 receptor of the present invention and a novel TNF ligand-like protein (HUVEO19) for TNF-α or TNF-β. Purified native TR1 receptor protein (100 µl/well) was added to wells of a 96-well plate, and incubated for 2 hr. After incubation, the plate was washed three times, 10 ng of either TNF-α or TNF-β was added to the wells and the plate was incubated for an additional 2 hr followed by an additional three washes. In a duplicate plate, 10 ng of a novel TNF ligand-like protein (HUVEO19) was incubated first with native TR1 receptor and after the initial three washes, 10 ng of either TNF-α or TNF-β was added to the wells for the second incubation. For each plate, the wells were washed three times and phosphatase-labeled polyclonal antibody specific for either TNF-α or TNF-β (200 µl) was added. After a further 2 hr incubation, the wells were washed three times wash times and 200 µl of substrate solution was added to each well. The plates were then incubated for 1 hr and the O.D. was measured using a ELISA reader (test wavelength 450 nm, correction wavelength 590 nm). All reagents were obtained from R & D System, as above.
Figure 8:
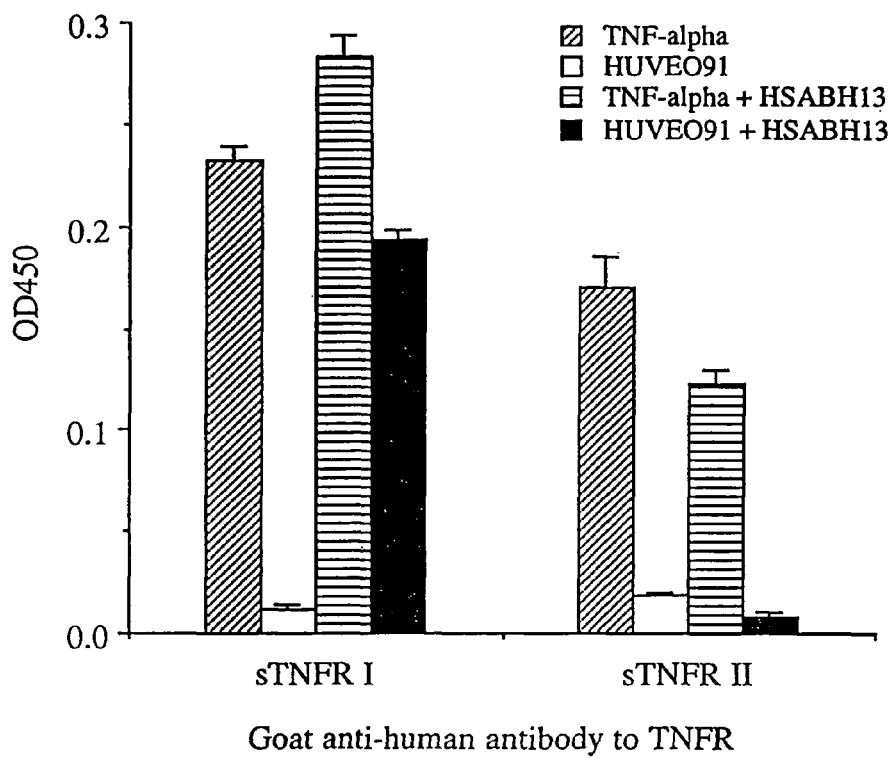
FIG. 8 shows a competitive binding assay between the native TR1 receptor of the present invention and human TNF-RI and TNF-RII for TNF-α and the novel TNF ligand-like protein described above. Purified native TR1 receptor protein (100 µl/well) was added to wells of a 96-well plate which was precoated with TNF-α or novel TNF ligand-like protein (HUVEO19), and incubated for 2 hr. After incubation, the plate was washed three times, 10 ng of either human TNF-RI or TNF-RII was added to the plate. The plate was then incubated for an additional 2 hr. After the 2 hr incubation, the wells were washed three times. In a duplicate plate, native TR1 receptor was omitted and 10 ng of either human TNF-RI or TNF-RII was added. After the second 2 hr incubation the plates were washed three times and phosphatase-labeled polyclonal antibody to human TNF-RI or TNF-RII (200 µl) was added to each well. After an additional 2 hr incubation, the plates were washed three times wash, 200 µl of substrate solution was added to each well, and plate was incubated for 1 hr. The O.D. was then measured using a ELISA reader (test wavelength 450 nm, correction wavelength 590 nm). All reagents were obtained from R & D System, as above.

Preferred, however, are nucleic acid molecules having sequences at least 90%, 95%, 96%, 97%, 98% or 99% identical to the nucleic acid sequence shown in FIG. 1 (SEQ ID NO:1), FIG. 2 (SEQ ID NO:3) or to the nucleic acid sequence of the deposited cDNA which do, in fact, encode a polypeptide having TR1 receptor protein activity. By "a polypeptide having TR1 receptor activity" is intended polypeptides exhibiting activity similar, but not necessarily identical, to an activity of the TR1 receptor protein of the invention (either the full-length protein or, preferably, the mature protein), as measured in a particular biological assay. For example, TR1 receptor protein activity can be measured using the binding affinity for a TR1-β ligand or other molecule shown to bind to the native TR1 receptor protein. For example, the competitive binding assays shown in FIG. 7 can be used to determine whether a candidate polypeptide has a binding affinity similar to that of the native TR1 receptor described herein.

Thus, "a polypeptide having TR1 receptor protein activity" includes polypeptides that exhibit TR1 receptor binding activity in the above-described assay. Although the degree of binding activity need not be identical to that of the TR1 receptor protein, preferably, "a polypeptide having TR1 receptor protein activity" will exhibit substantially similar activity as compared to the native TR1 receptor protein.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 1 (SEQ ID NO:1) or FIG. 2 (SEQ ID NO:3) will encode a polypeptide "having TR1 receptor protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having TR1 receptor protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie et al., "Deciphering the Message in Protein Sequences: Tolerance to Amino Acid Substitutions," Science 247:1306-1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie et al., Science 247:1306-1310 (1990), and the references cited therein.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

TR1 Receptor Polypeptides and Fragments

The present invention further relates to a polypeptide which has the deduced amino acid sequence of FIG. 1 (SEQ ID NO:2), FIG. 2 (SEQ ID NO:4), or which has the amino acid sequence encoded by the deposited cDNA, as well as fragments, analogs and derivatives of such a polypeptide.

The terms "fragment," "derivative" and "analog" when referring to the polypeptide of FIG. 1 (SEQ ID NO:2), FIG. 2 (SEQ ID NO:4), or that encoded by the deposited cDNA, means a polypeptide which retains essentially the same biological function or activity as such a polypeptide. Thus, an analog includes a proprotein which can be activated by cleavage of the proprotein portion to produce an active mature polypeptide.

The polypeptides of the present invention may be recombinant polypeptides, a natural polypeptides or synthetic polypeptides, preferably recombinant polypeptides.

It will be recognized in the art that some amino acid sequences of the TR1 receptor polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the TR1 receptor polypeptide which show substantial TR1 receptor polypeptide activity or which include regions of TR1 receptor protein such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie et al., supra.

Thus, the fragment, derivative or analog of the polypeptide of FIG. 1 (SEQ ID NO:2), FIG. 2 (SEQ ID NO:4), or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the TR1 receptor proteins. The prevention of aggregation is highly desirable. Aggregation of proteins not only results in a loss of activity but can also be problematic when preparing pharmaceutical formulations, because they can be immunogenic. (Pinckard et al., Clin Exp. Immunol. 2:331-340 (1967); Robbins et al., Diabetes 36:838-845 (1987); Cleland et al. Crit. Rev. Therapeutic Drug Carrier Systems 10:307-377 (1993)).

The replacement of amino acids can also change the selectivity of binding to cell surface receptors. Ostade et al., Nature 361:266-268 (1993) describes certain mutations resulting in selective binding of TNF-α to only one of the two known types of TNF receptors. Thus, the TR1 receptors of the present invention may include one or more amino acid substitutions, deletions or additions, either from natural mutations or human manipulation.

Changes are preferably of a minor nature, such as conservative amino acid substitutions that do not significantly affect the folding or activity of the protein (see Table 1).

TABLE 1

| Conservative Amino Acid Substitutions. | |
| --- | --- |
| Aromatic | Phenylalanine |
| | Tryptophan |
| | Tyrosine |
| Hydrophobic | Leucine |
| | Isoleucine |
| | Valine |

TABLE 1-continued

Conservative Amino Acid Substitutions.

| | |
|---|---|
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the TR1 receptors of the present invention that are essential for function can be identified by methods known in the art, such as site-directed mutagenesis or alanine-scanning mutagenesis (Cunningham and Wells, *Science* 244: 1081-1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

The polypeptides and polynucleotides of the present invention are preferably provided in an isolated form, and preferably are purified to homogeneity. A recombinantly produced version of the TR1 receptor polypeptide can be substantially purified by the one-step method described in Smith and Johnson, *Gene* 67:31-40 (1988).

The polypeptides of the present invention include the polypeptide encoded by the deposited cDNA including the leader, the mature polypeptide encoded by the deposited cDNA minus the leader (i.e., the mature protein), the polypeptide of FIG. 1 (SEQ ID NO:2) or FIG. 2 (SEQ ID NO:4) including the leader, the polypeptide of FIG. 1 (SEQ ID NO:2) or FIG. 2 (SEQ ID NO:4) minus the leader, as well as polypeptides which have at least 90% similarity, more preferably at least 95% similarity, and still more preferably at least 96%, 97%, 98% or 99% similarity to those described above. Further polypeptides of the present invention include polypeptides at least 80% identical, more preferably at least 90% or 95% identical, still more preferably at least 96%, 97%, 98% or 99% identical to the polypeptide encoded by the deposited cDNA, to the polypeptide of FIG. 1 (SEQ ID NO:2), the polypeptide of FIG. 2 (SEQ ID NO:4), and also include portions of such polypeptides with at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide. By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Advances in Applied Mathematics* 2:482-489, 1981) to find the best segment of similarity between two sequences.

By a polypeptide having an amino acid sequence at least, for example, 95% "identical" to a reference amino acid sequence of a TR1 receptor polypeptide is intended that the amino acid sequence of the polypeptide is identical to the reference sequence except that the polypeptide sequence may include up to five amino acid alterations per each 100 amino acids of the reference amino acid of the TR1 receptor polypeptides of the present invention. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIG. 1 (SEQ ID NO:2), FIG. 2 (SEQ ID NO:4), or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting. TR1 receptor protein expression as described below or as agonists and antagonists capable of enhancing or inhibiting TR1 receptor protein function. Further, such polypeptides can be used in the yeast two-hybrid system to "capture" TR1 receptor protein binding proteins which are also candidate agonist and antagonist according to the present invention. The yeast two hybrid system is described in Fields and Song, *Nature* 340:245-246 (1989).

As indicated, the above described TR1 receptor polypeptides are believed not to include a transmembrane domain. Thus, in an additional embodiment, the present invention relates to the TR1 receptor polypeptides of the present invention having an amino acid sequence further comprising a transmembrane domain. Such receptor polypeptides may be native or constructed from the TR1 receptors described herein according to recombinant techniques. Methods for isolating a nucleotide sequence encoding a TR1 receptor that contains a transmembrane domain include hybridizing nucleotide probes constructed from the sequence provided in FIG. 1 (SEQ ID NO:1) or FIG. 2 (SEQ ID NO:3) with a cDNA library obtained from one or more of the above described tissue sources.

If produced recombinantly or synthetically, suitable sites for the insertion of a transmembrane domain spanning amino acid sequence will be apparent to one skilled in the art. The present inventors have discovered that amino acid residues from about 22 to about 261, shown in FIG. 1 (SEQ ID NO:2), have considerable homology to the extracellular domain of human TR1-RII (FIG. 3; SEQ ID NO:5). Further, amino acid residues from about 262 to about 401, shown in FIG. 1 (SEQ ID NO:2), have considerable homology to the intracellular domain of human TR1-RII (FIG. 3; SEQ ID NO:5). Thus, one skilled in the art would appreciate that between amino acid residues 261 and 262 in either FIG. 1 (SEQ ID NO:2) or FIG. 2 (SEQ ID NO:4) (or a site proximal (within about 1-10 amino acids) thereto) would be a suitable site for the insertion of an amino acid sequence comprising a transmembrane domain. Polynucleotides encoding an amino acid sequence comprising a transmembrane domain may be isolated from (or constructed from the nucleotide sequence of) other TR1 receptor genes and inserted into an appropriate site of the deposited clone by recombinant techniques. Further, such domains may be synthetically constructed and inserted into the soluble TR1 receptors of the present invention. Insertion of such amino acid residues comprising a transmembrane domain into a TR1 receptor of the present invention would likely result in a non-soluble receptor that would integrate into membranes. A specific example of a transmembrane domain useful according to the present invention is the TNF-R2 transmembrane domain shown at amino acid residues from about 258 to about 287 in FIG. 3 (bottom sequence) (SEQ ID NO:5). Other such TR1 receptor transmembrane domains will be apparent to the those skilled in the art.

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe et al., *Science* 219:660-666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. Sutcliffe et al., supra, at 661. For instance, 18 of 20 peptides designed according to these guidelines, containing 8-39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., *Cell* 37:767-778 (1984. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides or peptides that can be used to generate TR1 receptor-specific antibodies include: a polypeptide comprising amino acid residues from about 20 to about 52 in FIG. 1 (SEQ ID NO:2) or FIG. 2 (SEQ ID NO:4); a polypeptide comprising amino acid residues from about 66 to about 203 in FIG. 1 (SEQ ID NO:2) or FIG. 2 (SEQ ID NO:4); a polypeptide comprising amino acid residues from about 229 to about 279 in FIG. 1 (SEQ ID NO:2) or FIG. 2 (SEQ ID NO:4); a polypeptide comprising amino acid residues from about 297 to about 378 in FIG. 1 (SEQ ID NO:2). As indicated above, the inventors have determined that the above polypeptide fragments are antigenic regions of the TR1 receptor protein.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10-20 mg of 248 different 13 residue peptides representing single amino acid variants of a segment of the HA1 polypeptide which were prepared and characterized (by ELISA-type binding studies) in less than four weeks. Houghten, *Proc. Natl. Acad. Sci. USA* 82:5131-5135 (1985). General method for the rapid solid-phase synthesis of large numbers of peptides: specificity of antigen-antibody interaction at the level of individual amino acids. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500-1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al., supra; Chow et al., *Proc. Natl. Acad. Sci. USA* 82:910-914; and Bittle et al., *J. Gen. Virol.* 66:2347-2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 μg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten. et al. (1996) on Peralkylated Oligopeptide Mixtures discloses linear $C_1$-$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "TR1 Receptor Polypeptides and Fragments" is hereby incorporated herein by reference.

As one of skill in the art will appreciate, TR1 receptor polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84-86 (1988)). Fusion proteins that have a disulfide-linked dimeric structure due to the IgG part can also be more efficient in binding and neutralizing other molecules than the monomeric TR1 receptor protein or protein fragment alone (Fountoulakis et al., *J. Biochem* 270: 3958-3964 (1995)).

Vectors and Host Cells

The present invention also relates to vectors which include polynucleotides of the present invention, host cells which are genetically engineered with vectors of the invention and the production of polypeptides of the invention by recombinant techniques.

Host cells are genetically engineered (transduced, transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the nucleic acid sequences of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); pTRC99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lad, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin by 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide of the present invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps. The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5—has been fused with Fc portions for the purpose of high-throughput screening assays to identify antagonists of hIL-5. See, Bennett et al., *Journal of Molecular Recognition*, 8:52-58 (1995) and Johanson et al., *The Journal of Biological Chemistry*, 270(16): 9459-9471 (1995).

The TR1 receptor protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

TR1 Receptor: Use for Detection of Disease States

The inventors have shown that the TR1 receptor of the present invention binds both TNF-α and TNF-β but has a higher affinity for TNF-β. See FIG. 7. TNF-β, a potent ligand of the TNF receptor proteins, is known to be involved in a number of biological processes including lymphocyte development, tumor necrosis, induction of an antiviral state, activation of polymorphonuclear leukocytes, induction of class I major histocompatibility complex antigens on endothelial cells, induction of adhesion molecules on endothelium and growth hormone stimulation (Ruddle and Horner, *Prog. Allergy*, 40:162-182 (1988)). TNF-α, also a ligand of the TR1 receptors of the present invention, has been reported to have a role in the rapid necrosis of tumors, immunostimulation, autoimmune disease, graft rejection, producing an anti-viral response, septic shock, cerebral malaria, cytotoxicity, protection against deleterious effects of ionizing radiation produced during a course of chemotherapy, such as denaturation of enzymes, lipid peroxidation and DNA damage (Nata et al, *J. Immunol.* 136(7):2483 (1987)), growth regulation, vascular endothelium effects and metabolic effects. TNF-α also triggers endothelial cells to secrete various factors, including PAI-1, IL-1, GM-CSF and IL-6 to promote cell proliferation. In addition, TNF-α up-regulates various cell adhesion molecules such as E-Selectin, ICAM-1 and VCAM-1. TNF-α and the Fas ligand have also been shown to induce programmed cell death.

It is believed that certain tissues in mammals with specific cancers express significantly altered levels of the TR1 receptor protein and mRNA encoding the TR1 receptor protein when compared to a corresponding "standard" mammal, i.e., a mammal of the same species not having the cancer. For example, the inventors have found that osteosarcoma, ovarian carcinoma, monocyte leukemia, and lung emphysemia cells express the TR1 receptor protein of the present invention. Further, since this protein is secreted, it is believed that enhanced levels of the TR1 receptor protein can be detected in certain body fluids (e.g., sera, plasma, urine, and spinal fluid) from mammals with cancer when compared to sera from mammals of the same species not having the cancer. Thus, the invention provides a diagnostic method useful during tumor diagnosis and possibly other disease states, which involves assaying the expression level of the gene encoding the TR1 receptor protein in mammalian cells or body fluid and comparing the gene expression level with a standard TR1 receptor gene expression level, whereby an increase or decrease in the gene expression level over the standard is indicative of certain tumors.

Where a tumor diagnosis has already been made according to conventional methods, the present invention is useful as a prognostic indicator, whereby patients exhibiting significantly enhanced TR1 receptor gene expression will experience a worse clinical outcome relative to patients expressing the gene at a lower level.

By "assaying the expression level of the gene encoding the TR1 receptor protein" is intended qualitatively or quantitatively measuring or estimating the level of the TR1 receptor protein or the level of the mRNA encoding the TR1 receptor protein in a first biological sample either directly (e.g., by determining or estimating absolute protein level or mRNA level) or relatively (e.g., by comparing to the TR1 receptor protein level or mRNA level in a second biological sample).

Preferably, the TR1 receptor protein level or mRNA level in the first biological sample is measured or estimated and compared to a standard TR1 receptor protein level or mRNA level, the standard being taken from a second biological sample obtained from an individual not having the cancer. As will be appreciated in the art, once a standard TR1 receptor protein level or mRNA level is known, it can be used repeatedly as a standard for comparison.

By "biological sample" is intended any biological sample obtained from an individual, cell line, tissue culture, or other source which contains TR1 receptor protein or mRNA. Biological samples include mammalian body fluids (such as sera, plasma, urine, synovial fluid and spinal fluid) which contain secreted mature TR1 receptor protein, and thymus, prostate, heart, placenta, muscle, liver, spleen, lung, kidney and umbilical tissue. Methods for obtaining tissue biopsies and body fluids from mammals are well known in the art. Where the biological sample is to include mRNA, a tissue biopsy is the preferred source.

The present invention is useful for detecting cancer and other disease states in mammals. In particular the invention is useful during diagnosis of cancer resulting from the proliferation of osteoblastoma cells. As described in Example 7, Northern blot analysis has shown that osteoblastoma cells, in addition to a number of normal tissues, have been found to express the TR1 receptor of the present invention. This result, when coupled with the fact that synovial sarcoma cells do not produce detectable levels of TR1 receptor mRNA, indicates that the molecules provided by the present invention may be useful for both detecting certain disease states as well as providing a treatment for such states. Preferred mammals include monkeys, apes, cats, dogs, cows, pigs, horses, rabbits and humans. Particularly preferred are humans.

Total cellular RNA can be isolated from a biological sample using any suitable technique such as the single-step guanidinium-thiocyanate-phenol-chloroform method described in Chomczynski and Sacchi, *Anal. Biochem.* 162: 156-159 (1987). Levels of mRNA encoding the TR1 receptor protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Example 7 below and in Harada et al., *Cell* 63:303-312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. TR1 receptor protein cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably at least 15 bp in length.

S1 mapping can be performed as described in Fujita et al., *Cell* 49:357-367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the TR1 receptor protein). Northern blot analysis can be performed as described above.

Preferably, levels of mRNA encoding the TR1 receptor protein are assayed using the RT-PCR method described in Makino et al., *Technique* 2:295-301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the TR1 receptor protein)) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying TR1 receptor protein levels in a biological sample can occur using any art-known method. Preferred for assaying TR1 receptor protein levels in a biological sample are antibody-based techniques. For example, TR1 receptor protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of TR1 receptor protein for Western-blot or dot/slot assay (Jalkanen., et al., *J. Cell. Biol.* 101:976-985 (1985); Jalkanen, et al., *J Cell. Biol.* 105:3087-3096 (1987)). In this technique, which is based on the use of cationic solid phases, quantitation of TR1 receptor protein can be accomplished using isolated TR1 receptor protein as a standard. This technique can also be applied to body fluids. With these samples, a molar concentration of TR1 receptor protein will aid to set standard values of TR1 receptor protein content for different body fluids, like serum, plasma, urine, spinal fluid, etc. The normal appearance of TR1 receptor protein amounts can then be set using values from healthy individuals, which can be compared to those obtained from a test subject.

Thus, from above, the present invention further relates to a diagnostic assay which detects an altered level of a soluble form of the polypeptide of the present invention where an elevated level in a sample derived from a host is indicative of certain diseases.

Assays available to detect levels of soluble receptors are well known to those of skill in the art, for example, radioimmunoassays, competitive-binding assays, Western blot analysis, and preferably an ELISA assay may be employed.

An ELISA assay initially comprises preparing an antibody specific to an antigen to the polypeptide of the present invention, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumen. Next, the monoclonal antibody is incubated in the dish during which time the monoclonal antibodies attach to any proteins of the present invention which are attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of the protein of interest present in a given volume of patient sample when compared against a standard curve.

A competition assay may be employed wherein antibodies specific to the polypeptides of the present invention are attached to a solid support. Labeled TR1 receptor polypeptides, and a sample derived from the host are passed over the solid support and the amount of label detected attached to the solid support can be correlated to a quantity in the sample. The soluble form of the receptor may also be employed to identify agonists and antagonists.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying TR1 receptor protein levels in a biological sample obtained from an individual, TR1 receptor protein can also be detected in vivo by imaging. Antibody labels or markers for in vivo imaging of TR1 receptor protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A TR1 receptor protein-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for cancer. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain TR1 receptor protein. In vivo tumor imaging is described in S. W. Burchiel et al., "Immunopharmacokinetics of Radiolabelled Antibodies and Their Fragments" (Chapter 13 in *Tumor Imaging. The Radiochemical Detection of Cancer*, S. W. Burchiel and B. A. Rhodes, eds., Masson Publishing Inc. (1982)).

TR1 receptor-protein specific antibodies for use in the present invention can be raised against the intact TR1 receptor protein or an antigenic polypeptide fragment thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')$_2$ fragments) which are capable of specifically binding to TR1 receptor protein. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)). Thus, these fragments are preferred.

The antibodies of the present invention may be prepared by any of a variety of methods. For example, cells expressing the TR1 receptor protein or an antigenic fragment thereof can be administered to an animal in order to induce the production of sera containing polyclonal antibodies. In a preferred method, a preparation of TR1 receptor protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or TR1 receptor protein binding fragments thereof). Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., (1981) pp. 563-681). In general, such procedures involve immunizing an animal (preferably a mouse) with a TR1 receptor protein antigen or, more preferably, with a TR1 receptor protein-expressing cell. Suitable cells can be recognized by their capacity to bind anti-TR1 receptor protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Rockville, Md. After fusion, the resulting hybridoma cells are selectively maintained in HAT medium, and then cloned by limiting dilution as described by Wands et al. (*Gastroenterology* 80:225-232 (1981)). The hybridoma cells obtained through such a selection are then assayed to identify clones which secrete antibodies capable of binding the TR1 receptor protein antigen.

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

Alternatively, additional antibodies capable of binding to the TR1 receptor protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, TR1 receptor-protein specific antibodies are used to immunize an animal, preferably a mouse. The splenocytes of such an animal are then used to produce hybridoma cells, and the hybridoma cells are screened to identify clones which produce an antibody whose ability to bind to the TR1 receptor protein-specific antibody can be blocked by the TR1 receptor protein antigen. Such antibodies comprise anti-idiotypic antibodies to the TR1 receptor protein-specific antibody and can be used to immunize an animal to induce formation of further TR1 receptor protein-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, TR1 receptor protein-binding fragments can be produced through the application of recombinant DNA technology or through synthetic chemistry.

Where in vivo imaging is used to detect enhanced levels of TR1 receptor protein for tumor diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Further suitable labels for the TR1 receptor protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging (Perkins et al., *Eur. I Nucl. Med.* 10:296-301 (1985); Carasquillo et al., *J. Nucl. Med.* 28:281-287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., *J. Nucl. Med.* 28:861-870 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al., *Clin. Chim. Acta* 70:1-31 (1976), and Schurs et al., *Clin. Chim. Acta* 81:1-40 (1977). Coupling techniques mentioned in the latter are the glutaraldehyde method, the periodate method, the dimaleimide method, the m-maleimidobenzyl-N-hydroxy-succinimide ester method, all of which methods are incorporated by reference herein.

TR1 Receptor: Use for Screening for Agonists and Antagonists of TR1 Receptor Function In one aspect, the present invention is directed to a method for enhancing an activity (e.g. cell proliferation, hematopoietic development, apoptosis) of a TR1 receptor of the present invention, which involves administering to a cell which expresses a TR1 receptor polypeptide an effective amount of an agonist capable of increasing TR1 receptor mediated signaling. Preferably, TR1 receptor mediated signaling is increased to treat a disease.

In a further aspect, the present invention is directed to a method for inhibiting an activity of a TR1 receptor of the present invention, which involves administering to a cell which expresses the TR1 receptor polypeptide an effective amount of an antagonist capable of decreasing TR1 receptor mediated signaling. Preferably, TR1 receptor mediated signaling is decreased to also treat a disease.

By "agonist" is intended naturally occurring and synthetic compounds capable of enhancing or potentiating an activity of a TR1 receptor of the present invention. By "antagonist" is intended naturally occurring and synthetic compounds capable of inhibiting an activity of a TR1 receptor. Whether any candidate "agonist" or "antagonist" of the present invention can enhance or inhibit an activity can be determined using art-known TR1-family ligand/receptor cellular response assays, including those described in more detail below.

Another method involves screening for compounds which inhibit activation of the receptor polypeptide of the present invention by determining inhibition of binding of labeled ligand to cells which have the receptor on the surface thereof. Such a method would be especially useful for a TR1 receptor of the present invention which includes a transmembrane spanning amino acid sequence and involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Further screening assays for agonist and antagonist of the present invention are described in Tartaglia and Goeddel, *J. Biol. Chem.* 267(7):4304-4307 (1992)).

Thus, in a further aspect, a screening method is provided for determining whether a candidate agonist or antagonist is capable of enhancing or inhibiting a cellular response to a TR1 receptor ligand. The method involves contacting cells which express the TR1 receptor polypeptide with a candidate compound and a ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TR1 receptor ligand (e.g., determining or estimating an increase or decrease in T-cell proliferation or tritiated thymidine labeling). By the invention, a cell expressing the TR1 receptor polypeptide can be contacted with either an endogenous or exogenously administered receptor ligand.

Agonist according to the present invention include naturally occurring and synthetic compounds such as, for example, TNF family ligand peptide fragments, transforming growth factor β, neurotransmitters (such as glutamate, dopamine, N-methyl-D-aspartate), tumor suppressors (p53), cytolytic T-cells and antimetabolites. Preferred agonists include chemotherapeutic drugs such as, for example, cisplatin, doxorubicin, bleomycin, cytosine arabinoside, nitrogen mustard, methotrexate and vincristine. Others include ethanol and β-amyloid peptide. (*Science* 267:1457-1458 (1995)). Further preferred agonist include polyclonal and monoclonal antibodies raised against the TR1 receptor polypeptide, or a fragment thereof. Such agonist antibodies raised against a TNF-family receptors are disclosed in Tartaglia et al., *Proc. Natl. Acad. Sci. USA* 88:9292-9296 (1991); and Tartaglia and Goeddel, *J. Biol. Chem.* 267(7):4304-4307 (1992) See, also, PCT Application WO 94/09137.

Antagonist according to the present invention include naturally occurring and synthetic compounds such as, for example, the CD40 ligand, neutral amino acids, zinc, estrogen, androgens, viral genes (such as Adenovirus ElB, Baculovirusp35 and L4P, Cowpox virus crmA, Epstein-Barr virus BHRF1, LMP-1, African swine fever virus LMW5-HL, and Herpesvirus γ1 34.5), calpain inhibitors, cysteine protease inhibitors, and tumor promoters (such as PMA, Phenobarbital, and α-Hexachlorocyclohexane). Other antagonists include polyclonal and monoclonal antagonist antibodies raised against the TR1 receptor polypeptides or a fragment thereof. Such antagonist antibodies raised against a TNF-family receptor are described in Tartaglia and Goeddel, *J. Biol. Chem.* 267(7):4304-4307 (1992)); and Tartaglia et al., *Cell* 73:213-216 (1993). See, also, PCT Application WO 94/09137.

Other potential antagonists include antisense molecules. Antisense technology can be used to control gene expression through antisense DNA or RNA or through triple-helix formation. Antisense techniques are discussed, for example, in Okano, *J. Neurochem.* 56:560 (1991); Oligodeoxynucleotides as Antisense Inhibitors of Gene Expression, CRC Press, Boca Raton, Fla. (1988). Triple helix formation is discussed in, for instance Lee et al., *Nucleic Acids Research* 6:3073 (1979); Cooney et al., *Science* 241:456 (1988); and Dervan et al., *Science* 251:1360 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide. The oligonucleotides described above can also be delivered to cells such that the antisense RNA or DNA may be expressed in vivo to inhibit production of the receptor.

Further antagonist according to the present invention include soluble TR1 receptor fragments, e.g., TR1 receptor fragments that include the ligand binding domain from the extracellular region of the full length receptor. Such soluble forms of the receptor, which may be naturally occurring or synthetic, antagonize TR1 receptor mediated signaling by competing with the cell surface forms of the TR1 receptor for binding to TNF-family ligands. Thus, such antagonists include soluble forms of the receptor that contain the ligand binding domains of the polypeptides of the present invention.

As indicated polyclonal and monoclonal antibody agonist or antagonist according to the present invention can be raised according to the methods disclosed in Tartaglia and Goeddel, *J. Biol. Chem.* 267(7):4304-4307 (1992)); Tartaglia et al., *Cell* 73:213-216 (1993)), and PCT Application WO 94/09137. The term "antibody" (Ab) or "monoclonal antibody" (mAb) as used herein is meant to include intact molecules as well as fragments thereof (such as, for example, Fab and F(ab')$_2$ fragments) which are capable of binding an antigen. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)).

Antibodies according to the present invention may be prepared by any of a variety of methods using TR1 receptor immunogens of the present invention. As indicated, such TR1 receptor immunogens include the full length TR1 receptor polypeptide (which may or may not include the leader sequence) and TR1 receptor polypeptide fragments such as the ligand binding domain, the extracellular domain and the intracellular domain.

In a preferred method, antibodies according to the present invention are mAbs. Such mAbs can be prepared using hybridoma technology (Kohler and Millstein, *Nature* 256:495-497 (1975) and U.S. Pat. No. 4,376,110; Harlow et al., *Antibodies: A Laboratory Manual*, Cold Spring Harbor Laboratory Press, Cold Spring Harbor, N.Y., 1988; *Monoclonal Antibodies and Hybridomas: A New Dimension in Biological Analyses*, Plenum Press, New York, N.Y., 1980; Campbell, "Monoclonal Antibody Technology," In: *Laboratory Techniques in Biochemistry and Molecular Biology*, Volume 13 (Burdon et al., eds.), Elsevier, Amsterdam (1984)).

Thymocytes, which have been shown to express the TR1 receptor of the present invention, can be used in a proliferation assay to identify both ligands and potential agonists and antagonists to the polypeptide of the present invention. For example, thymus cells are disaggregated from tissue and grown in culture medium. Incorporation of DNA precursors such as $^3$H-thymidine or 5-bromo-2'-deoxyuridine (BrdU) is monitored as a parameter for DNA synthesis and cellular proliferation. Cells which have incorporated BrdU into DNA can be detected using a monoclonal antibody against BrdU and measured by an enzyme or fluorochrome-conjugated second antibody. The reaction is quantitated by fluorimetry or by spectrophotometry. Two control wells and an experimental well are set up. TNF-β is added to all wells, while soluble receptors of the present invention are added to the experimental well. Also added to the experimental well is a compound to be screened. The ability of the compound to be screened to inhibit the interaction of TNF-β with the receptor polypeptides of the present invention may then be quantified. In the case of the agonists, the ability of the compound to enhance this interaction is quantified.

A determination may be made whether a ligand not known to be capable of binding to the polypeptide of the present invention can bind thereto comprising contacting a mammalian cell comprising an isolated molecule encoding a polypeptide of the present invention with a ligand under conditions permitting binding of ligands known to bind thereto, detecting the presence of any bound ligand, and thereby determining whether such ligands bind to a polypeptide of the present invention. Also, a soluble form of the receptor may utilized in the above assay where it is secreted in to the extra-cellular medium and contacted with ligands to determine which will bind to the soluble form of the receptor.

Other agonist and antagonist screening procedures involve providing appropriate cells which express the receptor on the surface thereof. In particular, a polynucleotide encoding a polypeptide of the present invention is employed to transfect cells to thereby express the polypeptide. Such transfection may be accomplished by procedures as hereinabove described.

Thus, for example, such assay may be employed for screening for a receptor antagonist by contacting the cells which encode the polypeptide of the present invention with both the receptor ligand and a compound to be screened. Inhibition of the signal generated by the ligand indicates that a compound is a potential antagonist for the receptor, i.e., inhibits activation of the receptor.

Proteins and other compounds which bind the TR1 receptor domains are also candidate agonist and antagonist according to the present invention. Such binding compounds can be "captured" using the yeast two-hybrid system (Fields and Song, *Nature* 340:245-246 (1989). A modified version of the yeast two-hybrid system has been described by Roger Brent and his colleagues (Gyuris, et al., *Cell* 75:791-803 (1993); Zervos, et al., *Cell* 72:223-232 (1993)). Briefly, a domain of the TR1 receptor polypeptide is used as bait for binding compounds. Positives are then selected by their ability to grow on plates lacking leucine, and then further tested for their ability to turn blue on plates with X-gal, as previously described in great detail (Gyuris, et al., supra). Preferably, the yeast two-hybrid system is used according to the present invention to capture compounds which bind to either the TR1 receptor ligand binding domain or to the TR1 receptor intracellular domain. Such compounds are good candidate agonist and antagonist of the present invention. This system has been used previously to isolate proteins which bind to the intracellular domain of the p55 and p75 TNF receptors (WO 95/31544). Once amino acid sequences are identified which bind to the TR1 receptor, these sequences can be screened for agonist or antagonist activity using, for example, the thymocyte proliferation assay described above.

Another assay which can be performed to identify agonists and antagonists of the TR1 receptors of the present invention involves the use of combinatorial chemistry to produce random peptides which then can be screened for both binding affinity the TR1 receptors and agonistic or antagonistic effects. One such assay has recently been performed using random peptides expressed on the surface of a bacteriophage. Wu, *Nature Biotechnology* 14:429-431. In this instance a phage display library was produced which displayed a vast array of peptides on the surface of the phage. The phage of this library were then injected into mice and phage expressing peptides which bound to various organs were then identified. The DNA contained in the phage bound to the organs was then sequenced to identify peptide motifs which are capable of interacting with the surfaces of cells in each organ. One skilled in the art would recognize that such a random peptide library could also be screened for motifs which bind to the surface of the TR1 receptors of the present invention. After such motifs are identified, these peptides can then be screened for agonistic or antagonistic activity using the assays described herein.

Other screening techniques include the use of cells which express the polypeptide of the present invention (for example, transfected CHO cells) in a system which measures extracellular pH changes caused by receptor activation, for example, as described in *Science*, 246:181-296 (1989). In another example, potential agonists or antagonists may be contacted with a cell which expresses the polypeptide of the present invention and a second messenger response, e.g., signal transduction may be measured to determine whether the potential antagonist or agonist is effective.

TR1 receptor antagonists also include a small molecule which binds to and occupies the TR1 receptor thereby making the receptor inaccessible to ligands which bind thereto such that normal biological activity is prevented. Examples of small molecules include but are not limited to small peptides or peptide-like molecules.

The TR1 receptor agonists may be employed to stimulate ligand activities, such as inhibition of tumor growth and necrosis of certain transplantable tumors. The agonists may also be employed to stimulate cellular differentiation, for example, T-cell, fibroblasts and haemopoietic cell differentiation. Agonists to the TR1 receptor may also augment TR1's role in the host's defense against microorganisms and prevent related diseases (infections such as that from *L. monocytogenes*) and Chlamidiae. The agonists may also be employed to protect against the deleterious effects of ionizing radiation produced during a course of radiotherapy, such as denaturation of enzymes, lipid peroxidation, and DNA damage.

The agonists may also be employed to mediate an anti-viral response, to regulate growth, to mediate the immune response and to treat immunodeficiencies related to diseases such as HIV.

Antagonists to the TR1 receptor may be employed to treat autoimmune diseases, for example, graft versus host rejection and allograft rejection, and T-cell mediated autoimmune diseases. It has been shown that T-cell proliferation is stimulated via a type 2 TNF receptor. Accordingly, antagonizing the receptor may prevent the proliferation of T-cells and treat T-cell mediated autoimmune diseases.

The antagonists may also be employed to prevent apoptosis, which is the basis for diseases such as viral infection, rheumatoid arthritis, systemic lupus erythematosus, insulin-dependent diabetes mellitus, and graft rejection. Similarly, the antagonists may be employed to prevent cytotoxicity.

The antagonists to the TR1 receptor may also be employed to treat B cell cancers which are stimulated by TR1.

Antagonists to the TR1 receptor may also be employed to treat and/or prevent septic shock, which remains a critical clinical condition. Septic shock results from an exaggerated host response, mediated by protein factors such as TNF and IL-1, rather than from a pathogen directly. For example, lipopolysaccharides have been shown to elicit the release of TNF leading to a strong and transient increase of its serum concentration. TNF causes shock and tissue injury when administered in excessive amounts. Accordingly, it is believed that antagonists to the TR1 receptor will block the actions of TNF and treat/prevent septic shock. These antagonists may also be employed to treat meningococcemia in children which correlates with high serum levels of TNF.

Among other disorders which may be treated by the antagonists to TR1 receptors, there are included, inflammation which is mediated by TNF receptor ligands, and the bacterial infections cachexia and cerebral malaria. The TR1 receptor antagonists may also be employed to treat inflammation mediated by ligands to the receptor such as TNF. In addition, TR1 receptors may also be useful for providing treatment for AIDS in that TNF-β is involved in the development of lymphocytes.

Therapeutics: Modes of Administration

The soluble TR1 receptor and agonists and antagonists may be employed in combination with a suitable pharmaceutical carrier. Such compositions comprise a therapeutically effective amount of the soluble receptor or agonist or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the soluble form of the receptor and agonists and antagonists of the present invention may also be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The TR1 receptor polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman. et al., *Biopolymers* 22:547-556 (1983)), poly (2-hydroxyethyl methacrylate) (Langer et al., *J. Biomed. Mater. Res.* 15:167-277 (1981), and Langer, *Chem. Tech.* 12:98-105 (1982)), ethylene vinyl acetate (Langer et al., Id.) or poly-D-(−)-3-hydroxybutyric acid (EP 133,988). Sustained-release TR1 receptor polypeptide compositions also include liposomally entrapped TR1 receptor polypeptide. Liposomes containing TR1 receptor polypeptide are prepared by methods known per se: DE 3,218,121; Epstein et al., *Proc. Natl. Acad. Sci.* (*USA*) 82:3688-3692 (1985); Hwang et al., *Proc. Natl. Acad. Sci.* (*USA*) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal TR1 receptor polypeptide therapy.

For parenteral administration, in one embodiment, the TR1 receptor polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the TR1 receptor polypeptide uniformly and intimately with liquid carriers or finely divided solid carriers or both. Then, if necessary, the product is shaped into the desired formulation.

Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The TR1 receptor polypeptide is typically formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of TR1 receptor polypeptide salts.

TR1 receptor polypeptide to be used for therapeutic administration must be sterile. Sterility is readily accomplished by filtration through sterile filtration membranes (e.g., 0.2 micron membranes). Therapeutic TR1 receptor polypeptide compositions generally are placed into a container having a sterile access port, for example, an intravenous solution bag or vial having a stopper pierceable by a hypodermic injection needle.

TR1 receptor polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous TR1 receptor polypeptide solution, and the resulting mixture is lyophilized. The infusion solution is prepared by reconstituting the lyophilized TR1 receptor polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The TR1 receptor and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller et al., *Biotechniques,* 7 (9):980-990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy* 1:5-14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include nucleic acid sequences encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Chromosome Assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15-25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: A Manual of Basic Techniques, Pergamon Press, New York (1988).

For example, the present inventors have mapped the native TR1 gene at the chromosomal region 8q23-24.1.

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, et al., *Nucleic Acids Res.*, 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments. Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in the method of Graham and Van der, *Virology*, 52:456-457 (1973).

Example 1

Bacterial Expression and Purification of TR1 Receptor

The DNA sequence encoding TR1 receptor, ATCC Accession No. 75899, is initially amplified using PCR oligonucleotide primers corresponding to the 5' and 3' end sequences of the processed TR1 receptor nucleic acid sequence (minus the signal peptide sequence). Additional nucleotides corresponding to TR1 receptor gene are added to the 5' and 3' end sequences respectively. The 5' oligonucleotide primer has the sequence 5' GCCAGAGGATCCGAAACGTTTCCTC-CAAAGTAC 3' (SEQ ID NO. 6) and end contains a BamHI restriction enzyme site (bold). The 3' sequence 5' CGGCT-TCTAGAATTACCTATCATTTCTAAAAAT 3' (SEQ ID NO. 7) contains complementary sequences to a Hind III site (bold) and is followed by 18 nucleotides of TR1 receptor (FIG. 2). The restriction enzyme sites correspond to the restriction enzyme sites on the bacterial expression vector pQE-9 (Qiagen, Inc. Chatsworth, Calif.). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 is then digested with BamHI and XbaI. The amplified sequences are ligated into pQE-9 and are inserted in frame with the sequence encoding for the histidine tag and the RBS. The ligation mixture is then used to transform E. coli strain M15/rep 4 (Qiagen, Inc.) by the procedure described in Sambrook et al., Molecular Cloning: A Laboratory Manual, Cold Spring Laboratory Press, (1989). M15/rep4 contains multiple copies of the plasmid pREP4, which expresses the lad repressor and also confers kanamycin resistance (Kan$^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 µg/ml) and Kan (25 µg/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lad repressor, clearing the P/O leading to increased gene expression. Cells are grown an extra 3 to 4 hours. Cells are then harvested by centrifugation. The cell pellet is solubilized in the chaotropic agent 6 molar Guanidine HCl. After clarification, solubilized TR1 receptor is purified from this solution by chromatography on a Nickel-Chelate column under conditions that allow for tight binding by proteins containing the 6-His tag (Hochuli et al., J. Chromatography 411:177-184 (1984)). TR1 receptor (90% pure) is eluted from the column in 6 molar guanidine HCl pH 5.0 and for the purpose of renaturation adjusted to 3 molar guanidine HCl, 100 mM sodium phosphate, 10 mM glutathione (reduced) and 2 mM glutathione (oxidized). After incubation in this solution for 12 hours the protein is dialyzed to 10 mmolar sodium phosphate.

Example 2

Cloning and Expression of the Native and the Carboxy Terminal Modified TR1 Receptor Using the Baculovirus Expression System The DNA sequence encoding the full-length native TR1 receptor protein, ATCC Accession No. 75899, is amplified using PCR oligonucleotide primers corresponding to the 5' and 3' sequences of the gene. The 5' primer has the sequence 5' cgc GGA TCC gccatc ATGAACAAGTTGCTTG 3' (SEQ ID NO. 8) and contain a BamHI restriction site followed by the first 17 base pairs of the native TR1 receptor coding sequence in FIG. 1.

The 3' primer has the sequence 5' cgc GGT ACC CAAT-TGTGAGGAAACAG 3' (SEQ ID NO. 9) and contains a Asp718 restriction site and, in reverse orientation, a sequence complementary to nucleotides 1270 to 1286 in FIG. 1.

For the carboxy terminal modified TR1 receptor, the 5' rimer has the sequence 5' GCGCGGATCC ATGAACAAGTTGCTGTGCTGC 3' (SEQ ID NO. 10) and contains a BamHI restriction enzyme site (in bold) and which is just behind the first 21 nucleotides of the modified TR1 receptor gene (the initiation codon for translation "ATG" is underlined) shown in FIG. 2.

The 3' primer has the sequence 5' GCGCTCTAGATTAC-CTATCATTTCTAAAAATAAC 3' (SEQ ID NO. 11) and contains the cleavage site for the restriction endonuclease XbaI and 21 nucleotides complementary to the 3' sequence of the modified TR1 receptor gene shown in FIG. 2.

The amplified modified TR1 receptor sequences were isolated from a 1% agarose gel using a commercially available kit ("Geneclean", BIO 101 Inc., La Jolla, Calif.). The fragments were then digested with the endonucleases BamHI and XbaI and then purified again on a 1% agarose gel. This fragment is designated F2.

The vector pRG1 (modification of pVL941 vector, discussed below) was used for the expression of the TR1 receptor proteins using the baculovirus expression system (for review see: Summers and Smith, A Manual of Methods for Baculovirus Vectors and Insect Cell Culture Procedures, Texas Agricultural Experimental Station Bulletin No. 1555 (1987)). This expression vector contains the strong polyhedrin promoter of the Autographa californica nuclear polyhedrosis virus (AcMNPV) followed by the recognition sites for the restriction endonucleases BamHI and XbaI. The polyadenylation site of the simian virus (SV40) was used for efficient polyadenylation. For an easy selection of recombinant viruses the beta-galactosidase gene from E. coli was inserted in the same orientation as the polyhedrin promoter followed by the polyadenylation signal of the polyhedrin gene. The polyhedrin sequences were flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow and Summers, Virology 170: 31-39 (1989)

The plasmid was digested with the restriction enzymes BamHI and XbaI. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. E. coli HB101 cells were then transformed and cells identified that contained the plasmid (pBac TR1 receptor) with the TR1 receptor genes using the enzymes BamHI and XbaI. The sequence of the cloned fragment was confirmed by DNA sequencing.

5 µg of the plasmid pBac TR1 receptor was cotransfected with 1.0 µg of a commercially available linearized baculovirus ("BaculoGold™ baculovirus DNA", Pharmingen, San Diego, Calif.) using the lipofection method (Feigner et al., Proc. Natl. Acad. Sci. USA, 84:7413-7417 (1987)).

1 µg of BaculoGold™ virus DNA and 5 µg of the plasmid pBac TR1 receptors were mixed in a sterile well of a microtiter plate containing 50 µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg, Md.) was used which allows an easy isolation of blue stained plaques. (A detailed description of a "plaque assay" can also be found in the user's guide for insect cell culture and baculovirology distributed by Life Technologies Inc., Gaithersburg, Md., page 9-10).

Four days after the serial dilution, the viruses were added to the cells and blue stained plaques were picked with the tip of an Eppendorf pipette. The agar containing the recombinant viruses were then resuspended in an Eppendorf tube containing 200 µl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-TR1 receptor at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells are further incubated for 16 hours before they are harvested by centrifugation and the labelled proteins visualized by SDS-PAGE and autoradiography.

Example 3

Cloning and Expression in Mammalian Cells

Most of the vectors used for the transient expression of the TR1 receptor protein gene sequences in mammalian cells should carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of trancription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular signals can also be used (e.g., human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 283, H9 and Jurkat cells, mouse NIH13T3 and C127 cells, Cos 1, Cos 7 and CV1, African green monkey cells, quail QC1-3 cells, mouse L cells and Chinese hamster ovary cells.

Alternatively, the gene can be expressed in stable cell lines that contain the gene integrated into a chromosome. The so-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., *Biochem J* 227:277-279 (1991); Bebbington et al., *Bio/Technology* 10:169-175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology,* 438-447 (March, 1985)) plus a fragment of the CMV-enhancer (Boshart et al., *Cell* 41:521-530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Expression of Recombinant Native TR1 Receptor in COS Cells

The expression of plasmid, TR1 receptor HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire TR1 receptor precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (Wilson et al., *Cell* 37:767 (1984)). The infusion of HA tag to the target protein allows easy detection of the recombinant protein with an antibody that recognizes the HA epitope.

For the native TR1 receptor (FIG. 1), the plasmid construction strategy is described as follows:

The DNA sequence encoding native TR1 receptor, ATCC Accession No. 75899, is constructed by PCR using two primers: The 5' primer has the sequence 5' cgc GGA TCC gccatc ATGAACAAGTTGCTGTG 3' (SEQ ID NO. 12) and contains a BamHI restriction site followed by the first 17 base pairs of the native TR1 receptor coding sequence in FIG. 1.

The 3' primer has the sequence 5' cgc GGT ACC CAAT-TGTGAGGAAACAG 3' (SEQ ID NO. 13) and contains a Asp718 restriction site and, in reverse orientation, a sequence complementary to nucleotides 1270 to 1286 in FIG. 1.

Therefore, the PCR product contains a BamHI site, a TR1 receptor coding sequence followed by HA tag fused in frame, a translation termination stop codon next to the HA tag, and an Asp718 site. The PCR amplified DNA fragment and the vector, pcDNAI/Amp, are digested with BamHI and Asp718 restriction enzymes and ligated. The ligation mixture is transformed into *E. coli* strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant TR1 receptors, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the TR1 receptor HA protein is detected by radiolabelling and immunoprecipitation method (Harlow and Lane, Antibodies: A Laboratory Manual, Cold Spring Harbor Laboratory Press, (1988)). Cells are labeled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5) (Wilson et al., supra). Both cell lysate and culture media are precipitated with a HA specific monoclonal antibody. Proteins precipitated are analyzed on 15% SDS-PAGE gels.

Example 3(b)

Cloning and Expression of the Native Receptor in CHO Cells

The vector pC1 is used for the expression of native TR1 receptor protein. Plasmid pC1 is a derivative of the plasmid pSV2-dhfr [ATCC Accession No. 37146]. Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357-1370, Hamlin, J. L. and Ma, C. 1990, *Biochem. et Biophys. Acta,* 1097:107-143, Page, M. J. and Sydenham, M. A., *Biotechnology* 9:64-68 (1991)). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., *Molecular and Cellular Biology,* March 1985:438-4470) plus a fragment isolated from the enhancer of the immediate early gene of human cytomegalovirus (CMV) (Boshart et al., *Cell* 41:521-530, 1985). Downstream of the promoter are the following single restriction enzyme cleavage sites that allow the integration of the genes: BamHI, Pvull, and Nrul. Behind these cloning sites the plasmid contains translational stop codons in all three reading frames followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel.

The DNA sequence encoding the native TR1 receptor, ATCC 75899, is amplified using PCR oligonucleotide primers corresponding to the 5' and 3' sequences of the gene:

The 5' primer as the sequence 5' cgc GGA TCC gccatc ATGAACAAGTTGCTGTG 3' (SEQ ID NO. 14) and contains a BamHI restriction site followed by the first 17 base pairs of the native TR1 receptor coding sequence in FIG. 1.

The 3' primer has the sequence) 5' cgc GGT ACC CAAT-TGTGAGGAAACAG 3' (SEQ ID NO. 15) and contains a Asp718 restriction site and, in reverse orientation, a sequence complementary to nucleotides 1270 to 1286 in FIG. 1.

Inserted into an expression vector, as described below, the 5' end of the amplified fragment encoding human TR1 receptor provides an efficient signal peptide. An efficient signal for initiation of translation in eukaryotic cells, as described by Kozak, *Mol. Biol.* 196:947-950 (1987) is appropriately located in the vector portion of the construct.

The amplified fragments are isolated from a 1% agarose gel as described above and then digested with the endonucleases BamHI and Asp718 and then purified again on a 1% agarose gel.

The isolated fragment and the dephosphorylated vector are then ligated with T4 DNA ligase. *E. coli* HB101 cells are then transformed and bacteria identified that contained the plasmid pC1 inserted in the correct orientation using the restriction enzyme BamHI. The sequence of the inserted gene is confirmed by DNA sequencing.

Transfection of CHO-DHFR-Cells

Chinese hamster ovary cells lacking an active DHFR enzyme are used for transfection. 5 μg of the expression plasmid C1 are cotransfected with 0.5 μg of the plasmid pSVneo using the lipofecting method (Feigner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10-14 days. After this period, single clones are trypsinized and then seeded in 6-well petri dishes using different concentrations of methotrexate (25 nM, 50 nM, 100 nM, 200 nM, 400 nM). Clones growing at the highest concentrations of methotrexate are then transferred to new 6-well plates containing even higher concentrations of methotrexate (500 nM, 1 μM, 2 μM, 5 μM). The same procedure is repeated until clones grow at a concentration of 100 μM.

The expression of the desired gene product is analyzed by Western blot analysis and SDS-PAGE.

Example 4

Purification of Soluble Native TR1 Receptor

Analysis of the amino acid sequence of native TR1 receptor shows a relatively high theoretical pI. A chromatography procedure was developed based on this feature to capture this protein to cation exchange column (poros 50 HS) at pH 7.0 at which most of other proteins do not bind to the column. This single-step purification yields 80-90% pure protein from recombinant baculovirus infected Sf-9 cell supernatant. The purified protein was confirmed to be the TNF-receptor homolog by N-terminus amino acid sequence analysis. The TR1-receptor can be further purified to >95% purity through heparin binding chromatography.

Seventeen mg of purified soluble TR1-receptor was prepared from 2 liters of baculovirus supernatant. Two mg of protein was used for antibody production. See FIGS. 5-8.

Example 5

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier et al, *DNA,* 7:219-25 (1988)) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform *E. coli* strain HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM), with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product. Numerous modifications and variations of the present invention are possible in light of the above teachings and, therefore, within the scope of the appended claims, the invention may be practiced otherwise than as particularly described.

Example 6

Osteogenic Cell Proliferation Assay for TR1 Receptor Activity

An assay for proliferatory effect of candidate agonists and antagonists of TR1 receptor function was performed using osteobast cell line HG63 as follows: A two-fold serial dilution of purified native TR1 receptor protein starting from 1000 ng/ml was made in RPMI 1640 medium with 0.5 to 10% FBS. Adherent target cells were prepared from confluent cultures by trypsinization in PBS, and non-adherent target cells were harvested from stationary cultures and washed once with fresh medium. Target cells were suspended at $1 \times 10^5$ cells/ml in medium containing 0.5 FBS and 0.1 ml aliquots were dispensed into 96-well flat-bottomed microtiter plates containing 0.1 ml serially diluted test samples. Incubation was continued for 70 hr. The activity was quantified using an MTS [3(4,5-dimethyl-thiazoyl-2-yl) 5 (3-carboxymethoxyphenyl)-2-(4-sulfophenyl)-2H-tetrazolium)] Assay or any other assay for cell numbers and/or activity. The MTS assay was performed by the addition of 20 μl of MTS and phenazine methosulfate (PMS) solution to 96 well plates (Stock solution was prepared as described by Promega Technical Bulletin No. 169). During a 3 hr incubation, living cells convert the MTS into a the aqueous soluble formazan product. Wells with medium only (no cells) were processed in exactly the same manner as the rest of the wells and were used for blank controls. Wells with medium and cells were used as baseline controls. The absorbence at 490 nm was recorded using an ELISA reader and is proportional to the number of viable cells in the wells. Cell growth promotion (positive percentage) or inhibition (negative percentage), as a percentage compared to baseline control wells (variation between three baseline control well is less than 5%), calculated for each sample concentration, by the formula: O.D.experimental/O.D.baseline control X 100-100. All determinations were made in triplicate. Mean and SD were calculated by Microsoft Excel.

Example 7

Northern Blot Analysis

Northern blot analysis is carried out to examine TR1 receptor gene expression in human tissues. A cDNA probe containing the sequence shown in FIG. 1 was labeled with $^{32}P$ using the rediprime DNA labelling system from Amersham Life Science, according to manufacturer's instructions. Unincorporated nucleotide was removed from labled probe using CHROMA SPIN-100 (Clontech). Two human Multiple Tissue Northern (MTN) blots (one labaled as H for human tissue, the other labaled as $H_2$ for human immune system) containing approximately 2 mg of poly (A)+ RNA per lane from various human tissues were purchased from Clontech. Also used were two Celline blots containing 20 ng total RNA from different cell lines. Northern blotting was performed with the Expresshyb Hybridization Solution (PT1190-1) from Clontech according to the manufacture's manual.

Gene expression was detected in heart, placenta, lung, liver, and kidney tissue. Lower levels of the mRNA was detected in thymus, prostate, testis, ovary, and small intestine. Expression was also detected in osteoblastoma, smooth muscle, fibroblasts, ovarian cancer, venous endothelial cells, monocyte lukemia cells, liver cells, and lung emphysemia cells. Expression can also be detected in the following cell types: human hippocampus, kidney medulla, macrophage, osteoblasts, human pancreas tumor, fetal cochlea, and adult pulmonary.

The entire disclosure of all publications cited herein are hereby incorporated by reference.

What is claimed is:

1. An isolated polypeptide comprising at least 30 contiguous amino acids of SEQ ID NO:2.

2. The isolated polypeptide of claim 1, which comprises at least 50 contiguous amino acids of SEQ ID NO:2.

3. An isolated polypeptide encoded by a polynucleotide that hybridizes under stringent conditions to the polynucleotide of SEQ ID NO:1 or the complement thereof, said stringent conditions consisting of:
   (a) incubating overnight at 42° C. in a solution consisting of 50% formamide, 5×SSC., 50 mM sodium phosphate (pH 7.6), 5×Denhardt's solution, 10% dextran sulfate, and 20 µg/ml denatured, sheared salmon sperm DNA; and
   (b) washing at 65° C. in a solution of 0.1×SSC,
wherein, said polypeptide has at least one activity selected from:

(a) binds tumor necrosis factor (TNF)-α ligand;
   (b) binds TNF-β ligand; or
   (c) binds to an antibody having specificity for the polypeptide of SEQ ID NO:2.

4. An isolated polypeptide comprising an amino acid sequence selected from the group consisting of:
   (a) amino acids −21 to 380 of SEQ ID NO:2;
   (b) amino acids −20 to 380 of SEQ ID NO:2; and
   (c) amino acids 1 to 380 of SEQ ID NO:2.

5. The isolated polypeptide of claim 4, which has at least one activity selected from:
   (a) binds tumor necrosis factor (TNF)-α ligand;
   (b) binds TNF-β ligand; or
   (c) binds to an antibody having specificity for the polypeptide of SEQ ID NO:2.

6. The isolated polypeptide of claim 4, which comprises an amino acid sequence identical to amino acids −21 to 380 of SEQ ID NO:2.

7. The isolated polypeptide of claim 4, which comprises an amino acid sequence identical to amino acids −20 to 380 of SEQ ID NO:2.

8. The isolated polypeptide of claim 4, which comprises an amino acid sequence identical to amino acids 1 to 380 of SEQ ID NO:2.

9. An isolated mature tumor necrosis factor receptor 1 polypeptide comprising mature tumor necrosis factor receptor 1 encoded by the cDNA contained in ATCC Deposit No. 75899.

10. An isolated polypeptide comprising at least 30 contiguous amino acids of the amino acid sequence encoded by the cDNA contained in ATCC Deposit No. 75899.

11. The isolated polypeptide of claim 10, which comprises at least 50 contiguous amino acids of the amino acid sequence encoded by the cDNA contained in ATCC Deposit No. 75899.

* * * * *

UNITED STATES PATENT AND TRADEMARK OFFICE
CERTIFICATE OF CORRECTION

| | | |
|---|---|---|
| PATENT NO. | : 8,110,659 B1 | Page 1 of 1 |
| APPLICATION NO. | : 08/718737 | |
| DATED | : February 7, 2012 | |
| INVENTOR(S) | : Greene et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 5 years.

Signed and Sealed this
Fourth Day of November, 2014

Michelle K. Lee
*Deputy Director of the United States Patent and Trademark Office*